United States Patent [19]

Evans et al.

[11] Patent Number: 5,571,696

[45] Date of Patent: Nov. 5, 1996

[54] RECEPTORS

[75] Inventors: Ronald M. Evans, La Jolla; David J. Mangelsdorf, San Diego; Estelita S. Ong, San Diego; Anthony E. Oro, San Diego, all of Calif.; Uwe K. Borgmeyer, Hamburg, Germany; Vincent Giguere, Etobicoke, Canada; Tso-Pang Yao, San Diego, Calif.

[73] Assignee: The Salk Institute for Biological Studies, La Jolla, Calif.

[21] Appl. No.: 333,358

[22] Filed: Nov. 2, 1994

Related U.S. Application Data

[63] Continuation of Ser. No. 761,068, Sep. 17, 1991, abandoned.

[51] Int. Cl.$^6$ .............................. C12P 21/06; C12N 5/00; C12N 15/00; C07H 17/00
[52] U.S. Cl. .................. 435/69.1; 435/240.1; 435/320.1; 536/23.1; 536/23.4
[58] Field of Search .................................. 536/23.1, 23.4; 435/69.1, 69.7, 240.1, 320.1

[56] References Cited

U.S. PATENT DOCUMENTS

| | | |
|---|---|---|
| 4,981,784 | 1/1991 | Evans et al. |
| 5,071,773 | 12/1991 | Evans et al. |

FOREIGN PATENT DOCUMENTS

| | | |
|---|---|---|
| 0325849 | 8/1989 | European Pat. Off. |

OTHER PUBLICATIONS

Devereux et al., "A comprehensive set of sequence analysis programs for the VAX", Nucleic Acids Research vol. 12:387–395 1984).

Kwok et al., "Nucleotide Sequence of a Full–Length Complementary DNA Clone and Amino Acid Sequence of Human Phenylalanine Hydroxylase," Biochemistry vol. 24:556–561 (1985).

Nathans et al., "Molecular Genetics of Human Color Vision: The Genes Encoding Blue, Green, and Red Pigments", Science vol. 232:193–202 (1986).

Hamada et al., "H–2RIIBP, a member of the nuclear hormone receptor superfamily that binds to both the regulatory element of major histocompatibility class I genes and the estrogen response element," Proc. Natl. Acad. Sci. USA vol. 86:8289–8293 (1989).

Tautz and Pfeifle, "A non–radioactive in situ hybidization method for the localization of specific RNAs in Drosophila embryos reveals translational control of the segmentation gene hunchback," Chromosoma vol. 98:81–85 (1989).

Giguere et al., "Identification of a receptor for the morphogen retinoic acid," Nature vol. 330:624–629 (1987).

Evans, Ronald M., "The Steroid and Thyroid Hormone Receptor Superfamily," Science vol. 240:889–895 (1988).

Umesono et al 1991 Cell 65:1255–1266.

Umesono & Evans 1989 Cell 57:1139–1146.

Umesono et al. 1988 Nature 336:262–265.

*Primary Examiner*—Robert A. Wax
*Assistant Examiner*—K. Cochrane Carlson
*Attorney, Agent, or Firm*—Pretty, Schroeder, Brueggemann & Clark; Stephen E. Reiter; Robert T. Ramos

[57] ABSTRACT

Novel members of the steroid/thyroid superfamily of receptors are described. DNA sequences encoding same, expression vectors containing such DNA and host cells transformed with such expression vectors are also disclosed, as are methods for the expression of the novel receptors of the invention, and various uses thereof.

14 Claims, 1 Drawing Sheet

```
verht19    1                              349        1952
                                          352 verht3     1 ////////////////////////////383          1952
                                          349 verhr5     1 \\\\\\\\\\\\\\\\300                      1952
                              352
```

FIGURE 1

Correlation of XR1 Alternate Splicing Products

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1952 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR1 (VERHT19.SEQ)

( i x ) FEATURE:
        ( A ) NAME/KEY: CDS
        ( B ) LOCATION: 79..1725

( i x ) FEATURE:
        ( A ) NAME/KEY: misc_feature
        ( B ) LOCATION: 349..1952
        ( D ) OTHER INFORMATION: /product="Carboxy terminal portion
            of XR1 variant verht3"

( i x ) FEATURE:
        ( A ) NAME/KEY: misc_feature
        ( B ) LOCATION: 352..1952
        ( D ) OTHER INFORMATION: /product="Carboxy terminal portion
            of XR1 variant verhr5"

( x i ) SEQUENCE DESCRIPTION: SEQ ID NO:1:

```
GAATTCGGGG ACTCCATAGT ACACTGGGGC AAAGCACAGC CCCAGTTTCT GGAGGCAGAT        60

GGGTAACCAG GAAAAGGC ATG AAT GAG GGG GCC CCA GGA GAC AGT GAC TTA        111
                    Met Asn Glu Gly Ala Pro Gly Asp Ser Asp Leu
                     1               5                  10

GAG ACT GAG GCA AGA GTG CCG TGG TCA ATC ATG GGT CAT TGT CTT CGA        159
```

|     |     |     |     |     |     |     |     |     |     |     |     |     |     |     |     |
|-----|-----|-----|-----|-----|-----|-----|-----|-----|-----|-----|-----|-----|-----|-----|-----|
| Glu | Thr | Glu | Ala | Arg | Val | Pro | Trp | Ser | Ile | Met | Gly | His | Cys | Leu | Arg |
|     |     |     | 15  |     |     |     |     | 20  |     |     |     |     | 25  |     |     |

| ACT | GGA | CAG | GCC | AGA | ATG | TCT | GCC | ACA | CCC | ACA | CCT | GCA | GGT | GAA | GGA | 207 |
|-----|-----|-----|-----|-----|-----|-----|-----|-----|-----|-----|-----|-----|-----|-----|-----|-----|
| Thr | Gly | Gln | Ala | Arg | Met | Ser | Ala | Thr | Pro | Thr | Pro | Ala | Gly | Glu | Gly |     |
|     |     | 30  |     |     |     |     | 35  |     |     |     |     | 40  |     |     |     |     |

| GCC | AGA | AGC | TCT | TCA | ACC | TGT | AGC | TCC | CTG | AGC | AGG | CTG | TTC | TGG | TCT | 255 |
| Ala | Arg | Ser | Ser | Ser | Thr | Cys | Ser | Ser | Leu | Ser | Arg | Leu | Phe | Trp | Ser |     |
|     | 45  |     |     |     |     | 50  |     |     |     |     | 55  |     |     |     |     |     |

| CAA | CTT | GAG | CAC | ATA | AAC | TGG | GAT | GGA | GCC | ACA | GCC | AAG | AAC | TTT | ATT | 303 |
| Gln | Leu | Glu | His | Ile | Asn | Trp | Asp | Gly | Ala | Thr | Ala | Lys | Asn | Phe | Ile |     |
| 60  |     |     |     |     | 65  |     |     |     |     | 70  |     |     |     |     | 75  |     |

| AAT | TTA | AGG | GAG | TTC | TTC | TCT | TTT | CTG | CTC | CCT | GCA | TTG | AGA | AAA | GCT | 351 |
| Asn | Leu | Arg | Glu | Phe | Phe | Ser | Phe | Leu | Leu | Pro | Ala | Leu | Arg | Lys | Ala |     |
|     |     |     |     | 80  |     |     |     |     | 85  |     |     |     |     | 90  |     |     |

| CAA | ATT | GAA | ATT | ATT | CCA | TGC | AAG | ATC | TGT | GGA | GAC | AAA | TCA | TCA | GGA | 399 |
| Gln | Ile | Glu | Ile | Ile | Pro | Cys | Lys | Ile | Cys | Gly | Asp | Lys | Ser | Ser | Gly |     |
|     |     |     |     | 95  |     |     |     |     | 100 |     |     |     |     | 105 |     |     |

| ATC | CAT | TAT | GGT | GTC | ATT | ACA | TGT | GAA | GGC | TGC | AAG | GGC | TTT | TTC | AGG | 447 |
| Ile | His | Tyr | Gly | Val | Ile | Thr | Cys | Glu | Gly | Cys | Lys | Gly | Phe | Phe | Arg |     |
|     |     |     | 110 |     |     |     |     | 115 |     |     |     |     | 120 |     |     |     |

| AGA | AGT | CAG | CAA | AGC | AAT | GCC | ACC | TAC | TCC | TGT | CCT | CGT | CAG | AAG | AAC | 495 |
| Arg | Ser | Gln | Gln | Ser | Asn | Ala | Thr | Tyr | Ser | Cys | Pro | Arg | Gln | Lys | Asn |     |
|     | 125 |     |     |     |     | 130 |     |     |     |     | 135 |     |     |     |     |     |

| TGT | TTG | ATT | GAT | CGA | ACC | AGT | AGA | AAC | CGC | TGC | CAA | CAC | TGT | CGA | TTA | 543 |
| Cys | Leu | Ile | Asp | Arg | Thr | Ser | Arg | Asn | Arg | Cys | Gln | His | Cys | Arg | Leu |     |
| 140 |     |     |     |     | 145 |     |     |     |     | 150 |     |     |     |     | 155 |     |

| CAG | AAA | TGC | CTT | GCC | GTA | GGG | ATG | TCT | CGA | GAT | GCT | GTA | AAA | TTT | GGC | 591 |
| Gln | Lys | Cys | Leu | Ala | Val | Gly | Met | Ser | Arg | Asp | Ala | Val | Lys | Phe | Gly |     |
|     |     |     |     | 160 |     |     |     |     | 165 |     |     |     |     | 170 |     |     |

| CGA | ATG | TCA | AAA | AAG | CAG | AGA | GAC | AGC | TTG | TAT | GCA | GAA | GTA | CAG | AAA | 639 |
| Arg | Met | Ser | Lys | Lys | Gln | Arg | Asp | Ser | Leu | Tyr | Ala | Glu | Val | Gln | Lys |     |
|     |     |     | 175 |     |     |     |     | 180 |     |     |     |     | 185 |     |     |     |

| CAC | CGG | ATG | CAG | CAG | CAG | CAG | CGC | GAC | CAC | CAG | CAG | CAG | CCT | GGA | GAG | 687 |
| His | Arg | Met | Gln | Gln | Gln | Gln | Arg | Asp | His | Gln | Gln | Gln | Pro | Gly | Glu |     |
|     |     |     | 190 |     |     |     |     | 195 |     |     |     |     | 200 |     |     |     |

| GCT | GAG | CCG | CTG | ACG | CCC | ACC | TAC | AAC | ATC | TCG | GCC | AAC | GGG | CTG | ACG | 735 |
| Ala | Glu | Pro | Leu | Thr | Pro | Thr | Tyr | Asn | Ile | Ser | Ala | Asn | Gly | Leu | Thr |     |
| 205 |     |     |     |     | 210 |     |     |     |     | 215 |     |     |     |     |     |     |

| GAA | CTT | CAC | GAC | GAC | CTC | AGT | AAC | TAC | ATT | GAC | GGG | CAC | ACC | CCT | GAG | 783 |
| Glu | Leu | His | Asp | Asp | Leu | Ser | Asn | Tyr | Ile | Asp | Gly | His | Thr | Pro | Glu |     |
| 220 |     |     |     |     | 225 |     |     |     |     | 230 |     |     |     |     | 235 |     |

| GGG | AGT | AAG | GCA | GAC | TCC | GCC | GTC | AGC | AGC | TTC | TAC | CTG | GAC | ATA | CAG | 831 |
| Gly | Ser | Lys | Ala | Asp | Ser | Ala | Val | Ser | Ser | Phe | Tyr | Leu | Asp | Ile | Gln |     |
|     |     |     |     | 240 |     |     |     |     | 245 |     |     |     |     | 250 |     |     |

| CCT | TCC | CCA | GAC | CAG | TCA | GGT | CTT | GAT | ATC | AAT | GGA | ATC | AAA | CCA | GAA | 879 |
| Pro | Ser | Pro | Asp | Gln | Ser | Gly | Leu | Asp | Ile | Asn | Gly | Ile | Lys | Pro | Glu |     |
|     |     |     | 255 |     |     |     |     | 260 |     |     |     |     | 265 |     |     |     |

| CCA | ATA | TGT | GAC | TAC | ACA | CCA | GCA | TCA | GGC | TTC | TTT | CCC | TAC | TGT | TCG | 927 |
| Pro | Ile | Cys | Asp | Tyr | Thr | Pro | Ala | Ser | Gly | Phe | Phe | Pro | Tyr | Cys | Ser |     |
|     |     | 270 |     |     |     |     | 275 |     |     |     |     | 280 |     |     |     |     |

| TTC | ACC | AAC | GGC | GAG | ACT | TCC | CCA | ACT | GTG | TCC | ATG | GCA | GAA | TTA | GAA | 975 |
| Phe | Thr | Asn | Gly | Glu | Thr | Ser | Pro | Thr | Val | Ser | Met | Ala | Glu | Leu | Glu |     |
|     | 285 |     |     |     |     | 290 |     |     |     |     | 295 |     |     |     |     |     |

| CAC | CTT | GCA | CAG | AAT | ATA | TCT | AAA | TCG | CAT | CTG | GAA | ACC | TGC | CAA | TAC | 1023 |
| His | Leu | Ala | Gln | Asn | Ile | Ser | Lys | Ser | His | Leu | Glu | Thr | Cys | Gln | Tyr |      |
| 300 |     |     |     |     | 305 |     |     |     |     | 310 |     |     |     |     | 315 |      |

| TTG | AGA | GAA | GAG | CTC | CAG | CAG | ATA | ACG | TGG | CAG | ACC | TTT | TTA | CAG | GAA | 1071 |
| Leu | Arg | Glu | Glu | Leu | Gln | Gln | Ile | Thr | Trp | Gln | Thr | Phe | Leu | Gln | Glu |      |
|     |     |     |     | 320 |     |     |     |     | 325 |     |     |     |     | 330 |     |      |

| GAA | ATT | GAG | AAC | TAT | CAA | AAC | AAG | CAG | CGG | GAG | GTG | ATG | TGG | CAA | TTG | 1119 |

| | | | | | | | | | | | | | | | | |
|---|---|---|---|---|---|---|---|---|---|---|---|---|---|---|---|---|
| | Glu | Ile | Glu | Asn<br>335 | Tyr | Gln | Asn | Lys<br>340 | Gln | Arg | Glu | Val | Met | Trp<br>345 | Gln | Leu |

| TGT | GCC | ATC | AAA | ATT | ACA | GAA | GCT | ATA | CAG | TAT | GTG | GTG | GAG | TTT | GCC | 1167 |
|---|---|---|---|---|---|---|---|---|---|---|---|---|---|---|---|---|
| Cys | Ala | Ile<br>350 | Lys | Ile | Thr | Glu | Ala<br>355 | Ile | Gln | Tyr | Val | Val<br>360 | Glu | Phe | Ala | |

| AAA | CGC | ATT | GAT | GGA | TTT | ATG | GAA | CTG | TGT | CAA | AAT | GAT | CAA | ATT | GTG | 1215 |
|---|---|---|---|---|---|---|---|---|---|---|---|---|---|---|---|---|
| Lys | Arg<br>365 | Ile | Asp | Gly | Phe | Met<br>370 | Glu | Leu | Cys | Gln | Asn<br>375 | Asp | Gln | Ile | Val | |

| CTT | CTA | AAA | GCA | GGT | TCT | CTA | GAG | GTG | GTG | TTT | ATC | AGA | ATG | TGC | CGT | 1263 |
|---|---|---|---|---|---|---|---|---|---|---|---|---|---|---|---|---|
| Leu<br>380 | Leu | Lys | Ala | Gly | Ser<br>385 | Leu | Glu | Val | Val | Phe<br>390 | Ile | Arg | Met | Cys | Arg<br>395 | |

| GCC | TTT | GAC | TCT | CAG | AAC | AAC | ACC | GTG | TAC | TTT | GAT | GGG | AAG | TAT | GCC | 1311 |
|---|---|---|---|---|---|---|---|---|---|---|---|---|---|---|---|---|
| Ala | Phe | Asp | Ser | Gln<br>400 | Asn | Asn | Thr | Val | Tyr<br>405 | Phe | Asp | Gly | Lys | Tyr<br>410 | Ala | |

| AGC | CCC | GAC | GTC | TTC | AAA | TCC | TTA | GGT | TGT | GAA | GAC | TTT | ATT | AGC | TTT | 1359 |
|---|---|---|---|---|---|---|---|---|---|---|---|---|---|---|---|---|
| Ser | Pro | Asp | Val<br>415 | Phe | Lys | Ser | Leu | Gly<br>420 | Cys | Glu | Asp | Phe | Ile<br>425 | Ser | Phe | |

| GTG | TTT | GAA | TTT | GGA | AAG | AGT | TTA | TGT | TCT | ATG | CAC | CTG | ACT | GAA | GAT | 1407 |
|---|---|---|---|---|---|---|---|---|---|---|---|---|---|---|---|---|
| Val | Phe | Glu<br>430 | Phe | Gly | Lys | Ser | Leu<br>435 | Cys | Ser | Met | His | Leu<br>440 | Thr | Glu | Asp | |

| GAA | ATT | GCA | TTA | TTT | TCT | GCA | TTT | GTA | CTG | ATG | TCA | GCA | GAT | CGC | TCA | 1455 |
|---|---|---|---|---|---|---|---|---|---|---|---|---|---|---|---|---|
| Glu | Ile | Ala<br>445 | Leu | Phe | Ser | Ala | Phe<br>450 | Val | Leu | Met | Ser<br>455 | Ala | Asp | Arg | Ser | |

| TGG | CTG | CAA | GAA | AAG | GTA | AAA | ATT | GAA | AAA | CTG | CAA | CAG | AAA | ATT | CAG | 1503 |
|---|---|---|---|---|---|---|---|---|---|---|---|---|---|---|---|---|
| Trp<br>460 | Leu | Gln | Glu | Lys | Val<br>465 | Lys | Ile | Glu | Lys | Leu<br>470 | Gln | Gln | Lys | Ile | Gln<br>475 | |

| CTA | GCT | CTT | CAA | CAC | GTC | CTA | CAG | AAG | AAT | CAC | CGA | GAA | GAT | GGA | ATA | 1551 |
|---|---|---|---|---|---|---|---|---|---|---|---|---|---|---|---|---|
| Leu | Ala | Leu | Gln | His<br>480 | Val | Leu | Gln | Lys | Asn<br>485 | His | Arg | Glu | Asp | Gly<br>490 | Ile | |

| CTA | ACA | AAG | TTA | ATA | TGC | AAG | GTG | TCT | ACA | TTA | AGA | GCC | TTA | TGT | GGA | 1599 |
|---|---|---|---|---|---|---|---|---|---|---|---|---|---|---|---|---|
| Leu | Thr | Lys | Leu<br>495 | Ile | Cys | Lys | Val | Ser<br>500 | Thr | Leu | Arg | Ala | Leu<br>505 | Cys | Gly | |

| CGA | CAT | ACA | GAA | AAG | CTA | ATG | GCA | TTT | AAA | GCA | ATA | TAC | CCA | GAC | ATT | 1647 |
|---|---|---|---|---|---|---|---|---|---|---|---|---|---|---|---|---|
| Arg | His | Thr<br>510 | Glu | Lys | Leu | Met | Ala<br>515 | Phe | Lys | Ala | Ile | Tyr<br>520 | Pro | Asp | Ile | |

| GTG | CGA | CTT | CAT | TTT | CCT | CCA | TTA | TAC | AAG | GAG | TTG | TTC | ACT | TCA | GAA | 1695 |
|---|---|---|---|---|---|---|---|---|---|---|---|---|---|---|---|---|
| Val | Arg<br>525 | Leu | His | Phe | Pro | Pro<br>530 | Leu | Tyr | Lys | Glu | Leu<br>535 | Phe | Thr | Ser | Glu | |

| TTT | GAG | CCA | GCA | ATG | CAA | ATT | GAT | GGG | TAAATGTTAT | CACCTAAGCA | 1742 |
|---|---|---|---|---|---|---|---|---|---|---|---|
| Phe<br>540 | Glu | Pro | Ala | Met | Gln<br>545 | Ile | Asp | Gly | | | |

| CTTCTAGAAT | GTCTGAAGTA | CAAACATGAA | AAACAAACAA | AAAAATTAAC | CGAGACACTT | 1802 |
|---|---|---|---|---|---|---|
| TATATGGCCC | TGCACAGACC | TGGAGCGCCA | CACACTGCAC | ATCTTTTGGT | GATCGGGGTC | 1862 |
| AGGCAAAGGA | GGGGAAACAA | TGAAAACAAA | TAAAGTTGAA | CTTGTTTTTC | TCAAAAAAAA | 1922 |
| AAAAAAAAAA | AAAAAAAAAA | AAAAAAAAA | | | | 1952 |

( 2 ) INFORMATION FOR SEQ ID NO:2:

( i ) SEQUENCE CHARACTERISTICS:
        ( A ) LENGTH: 548 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asn | Glu | Gly | Ala | Pro | Gly | Asp | Ser | Asp | Leu | Glu | Thr | Glu | Ala | Arg |
|---|---|---|---|---|---|---|---|---|---|---|---|---|---|---|---|
| 1 | | | | 5 | | | | | 10 | | | | | 15 | |

| Val | Pro | Trp | Ser | Ile | Met | Gly | His | Cys | Leu | Arg | Thr | Gly | Gln | Ala | Arg |
|---|---|---|---|---|---|---|---|---|---|---|---|---|---|---|---|
| | | | 20 | | | | | 25 | | | | | 30 | | |

Met Ser Ala Thr Pro Thr Pro Ala Gly Glu Gly Ala Arg Ser Ser Ser
                35                  40                  45

Thr Cys Ser Ser Leu Ser Arg Leu Phe Trp Ser Gln Leu Glu His Ile
        50                  55                  60

Asn Trp Asp Gly Ala Thr Ala Lys Asn Phe Ile Asn Leu Arg Glu Phe
65                      70                  75                  80

Phe Ser Phe Leu Leu Pro Ala Leu Arg Lys Ala Gln Ile Glu Ile Ile
                85                      90                      95

Pro Cys Lys Ile Cys Gly Asp Lys Ser Ser Gly Ile His Tyr Gly Val
                100                 105                 110

Ile Thr Cys Glu Gly Cys Lys Gly Phe Phe Arg Arg Ser Gln Gln Ser
        115                 120                 125

Asn Ala Thr Tyr Ser Cys Pro Arg Gln Lys Asn Cys Leu Ile Asp Arg
    130                 135                 140

Thr Ser Arg Asn Arg Cys Gln His Cys Arg Leu Gln Lys Cys Leu Ala
145                 150                 155                 160

Val Gly Met Ser Arg Asp Ala Val Lys Phe Gly Arg Met Ser Lys Lys
                165                 170                 175

Gln Arg Asp Ser Leu Tyr Ala Glu Val Gln Lys His Arg Met Gln Gln
            180                 185                 190

Gln Gln Arg Asp His Gln Gln Gln Pro Gly Glu Ala Glu Pro Leu Thr
            195                 200                 205

Pro Thr Tyr Asn Ile Ser Ala Asn Gly Leu Thr Glu Leu His Asp Asp
    210                 215                 220

Leu Ser Asn Tyr Ile Asp Gly His Thr Pro Glu Gly Ser Lys Ala Asp
225                 230                 235                 240

Ser Ala Val Ser Ser Phe Tyr Leu Asp Ile Gln Pro Ser Pro Asp Gln
                245                 250                 255

Ser Gly Leu Asp Ile Asn Gly Ile Lys Pro Glu Pro Ile Cys Asp Tyr
            260                 265                 270

Thr Pro Ala Ser Gly Phe Phe Pro Tyr Cys Ser Phe Thr Asn Gly Glu
        275                 280                 285

Thr Ser Pro Thr Val Ser Met Ala Glu Leu Glu His Leu Ala Gln Asn
    290                 295                 300

Ile Ser Lys Ser His Leu Glu Thr Cys Gln Tyr Leu Arg Glu Glu Leu
305                 310                 315                 320

Gln Gln Ile Thr Trp Gln Thr Phe Leu Gln Glu Glu Ile Glu Asn Tyr
                325                 330                 335

Gln Asn Lys Gln Arg Glu Val Met Trp Gln Leu Cys Ala Ile Lys Ile
            340                 345                 350

Thr Glu Ala Ile Gln Tyr Val Val Glu Phe Ala Lys Arg Ile Asp Gly
            355                 360                 365

Phe Met Glu Leu Cys Gln Asn Asp Gln Ile Val Leu Leu Lys Ala Gly
    370                 375                 380

Ser Leu Glu Val Val Phe Ile Arg Met Cys Arg Ala Phe Asp Ser Gln
385                 390                 395                 400

Asn Asn Thr Val Tyr Phe Asp Gly Lys Tyr Ala Ser Pro Asp Val Phe
                405                 410                 415

Lys Ser Leu Gly Cys Glu Asp Phe Ile Ser Phe Val Phe Glu Phe Gly
            420                 425                 430

Lys Ser Leu Cys Ser Met His Leu Thr Glu Asp Glu Ile Ala Leu Phe
        435                 440                 445

Ser Ala Phe Val Leu Met Ser Ala Asp Arg Ser Trp Leu Gln Glu Lys

|     | 450 |     |     |     | 455 |     |     |     | 460 |     |     |     |     |
|-----|-----|-----|-----|-----|-----|-----|-----|-----|-----|-----|-----|-----|-----|
| Val | Lys | Ile | Glu | Lys | Leu | Gln | Gln | Lys | Ile | Gln | Leu | Ala | Leu | Gln | His |
| 465 |     |     |     |     | 470 |     |     |     | 475 |     |     |     |     | 480 |

| Val | Leu | Gln | Lys | Asn | His | Arg | Glu | Asp | Gly | Ile | Leu | Thr | Lys | Leu | Ile |
|-----|-----|-----|-----|-----|-----|-----|-----|-----|-----|-----|-----|-----|-----|-----|-----|
|     |     |     |     | 485 |     |     |     | 490 |     |     |     |     |     | 495 |     |

| Cys | Lys | Val | Ser | Thr | Leu | Arg | Ala | Leu | Cys | Gly | Arg | His | Thr | Glu | Lys |
|-----|-----|-----|-----|-----|-----|-----|-----|-----|-----|-----|-----|-----|-----|-----|-----|
|     |     |     | 500 |     |     |     |     | 505 |     |     |     |     | 510 |     |     |

| Leu | Met | Ala | Phe | Lys | Ala | Ile | Tyr | Pro | Asp | Ile | Val | Arg | Leu | His | Phe |
|-----|-----|-----|-----|-----|-----|-----|-----|-----|-----|-----|-----|-----|-----|-----|-----|
|     |     | 515 |     |     |     |     | 520 |     |     |     |     | 525 |     |     |     |

| Pro | Pro | Leu | Tyr | Lys | Glu | Leu | Phe | Thr | Ser | Glu | Phe | Glu | Pro | Ala | Met |
|-----|-----|-----|-----|-----|-----|-----|-----|-----|-----|-----|-----|-----|-----|-----|-----|
|     | 530 |     |     |     |     | 535 |     |     |     |     | 540 |     |     |     |     |

| Gln | Ile | Asp | Gly |
|-----|-----|-----|-----|
| 545 |     |     |     |

( 2 ) INFORMATION FOR SEQ ID NO:3:

( i ) SEQUENCE CHARACTERISTICS:
        ( A ) LENGTH: 386 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: AMINO TERMINAL PORTION OF XR1PRIME
        ( VERHT3 . SEQ )

( i x ) FEATURE:
        ( A ) NAME/KEY: CDS
        ( B ) LOCATION: 90..386

( x i ) SEQUENCE DESCRIPTION: SEQ ID NO:3:

| CCATCTGTCT | GATCACCTTG | GACTCCATAG | TACACTGGGG | CAAAGCACAG | CCCCAGTTTC | | | | | 60 |
|---|---|---|---|---|---|---|---|---|---|---|

| TGGAGGCAGA | TGGGTAACCA | GGAAAAGGC | ATG | AAT | GAG | GGG | GCC | CCA | GGA | GAC | 113 |
|---|---|---|---|---|---|---|---|---|---|---|---|
|   |   |   | Met | Asn | Glu | Gly | Ala | Pro | Gly | Asp |   |
|   |   |   | 1 |   |   |   | 5 |   |   |   |   |

| AGT | GAC | TTA | GAG | ACT | GAG | GCA | AGA | GTG | CCG | TGG | TCA | ATC | ATG | GGT | CAT | 161 |
|---|---|---|---|---|---|---|---|---|---|---|---|---|---|---|---|---|
| Ser | Asp | Leu | Glu | Thr | Glu | Ala | Arg | Val | Pro | Trp | Ser | Ile | Met | Gly | His |  |
|  | 10 |  |  |  | 15 |  |  |  |  | 20 |  |  |  |  |  |  |

| TGT | CTT | CGA | ACT | GGA | CAG | GCC | AGA | ATG | TCT | GCC | ACA | CCC | ACA | CCT | GCA | 209 |
|---|---|---|---|---|---|---|---|---|---|---|---|---|---|---|---|---|
| Cys | Leu | Arg | Thr | Gly | Gln | Ala | Arg | Met | Ser | Ala | Thr | Pro | Thr | Pro | Ala |  |
| 25 |  |  |  | 30 |  |  |  |  | 35 |  |  |  |  |  | 40 |  |

| GGT | GAA | GGA | GCC | AGA | AGG | GAT | GAA | CTT | TTT | GGG | ATT | CTC | CAA | ATA | CTC | 257 |
|---|---|---|---|---|---|---|---|---|---|---|---|---|---|---|---|---|
| Gly | Glu | Gly | Ala | Arg | Arg | Asp | Glu | Leu | Phe | Gly | Ile | Leu | Gln | Ile | Leu |  |
|  |  |  |  | 45 |  |  |  |  | 50 |  |  |  |  | 55 |  |  |

| CAT | CAG | TGT | ATC | CTG | TCT | TCA | GGT | GAT | GCT | TTT | GTT | CTT | ACT | GGC | GTC | 305 |
|---|---|---|---|---|---|---|---|---|---|---|---|---|---|---|---|---|
| His | Gln | Cys | Ile | Leu | Ser | Ser | Gly | Asp | Ala | Phe | Val | Leu | Thr | Gly | Val |  |
|  |  |  | 60 |  |  |  |  | 65 |  |  |  |  | 70 |  |  |  |

| TGT | TGT | TCC | TGG | AGG | CAG | AAT | GGC | AAG | CCA | CCA | TAT | TCA | CAA | AAG | GAA | 353 |
|---|---|---|---|---|---|---|---|---|---|---|---|---|---|---|---|---|
| Cys | Cys | Ser | Trp | Arg | Gln | Asn | Gly | Lys | Pro | Pro | Tyr | Ser | Gln | Lys | Glu |  |
|  |  | 75 |  |  |  |  | 80 |  |  |  |  | 85 |  |  |  |  |

| GAT | AAG | GAA | GTA | CAA | ACT | GGA | TAC | ATG | AAT | GCT | 386 |
|---|---|---|---|---|---|---|---|---|---|---|---|
| Asp | Lys | Glu | Val | Gln | Thr | Gly | Tyr | Met | Asn | Ala |  |
|  | 90 |  |  |  | 95 |  |  |  |  |  |  |

( 2 ) INFORMATION FOR SEQ ID NO:4:

( i ) SEQUENCE CHARACTERISTICS:
        ( A ) LENGTH: 99 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Asn | Glu | Gly | Ala | Pro | Gly | Asp | Ser | Asp | Leu | Glu | Thr | Glu | Ala | Arg |
|---|---|---|---|---|---|---|---|---|---|---|---|---|---|---|---|
| 1 | | | | 5 | | | | | 10 | | | | | 15 | |

| Val | Pro | Trp | Ser | Ile | Met | Gly | His | Cys | Leu | Arg | Thr | Gly | Gln | Ala | Arg |
|---|---|---|---|---|---|---|---|---|---|---|---|---|---|---|---|
| | | | 20 | | | | | 25 | | | | | 30 | | |

| Met | Ser | Ala | Thr | Pro | Thr | Pro | Ala | Gly | Glu | Gly | Ala | Arg | Arg | Asp | Glu |
|---|---|---|---|---|---|---|---|---|---|---|---|---|---|---|---|
| | | 35 | | | | | 40 | | | | | 45 | | | |

| Leu | Phe | Gly | Ile | Leu | Gln | Ile | Leu | His | Gln | Cys | Ile | Leu | Ser | Ser | Gly |
|---|---|---|---|---|---|---|---|---|---|---|---|---|---|---|---|
| | 50 | | | | | 55 | | | | | 60 | | | | |

| Asp | Ala | Phe | Val | Leu | Thr | Gly | Val | Cys | Cys | Ser | Trp | Arg | Gln | Asn | Gly |
|---|---|---|---|---|---|---|---|---|---|---|---|---|---|---|---|
| 65 | | | | | 70 | | | | | 75 | | | | | 80 |

| Lys | Pro | Pro | Tyr | Ser | Gln | Lys | Glu | Asp | Lys | Glu | Val | Gln | Thr | Gly | Tyr |
|---|---|---|---|---|---|---|---|---|---|---|---|---|---|---|---|
| | | | | 85 | | | | | 90 | | | | | 95 | |

Met Asn Ala ( 2 ) INFORMATION FOR SEQ ID NO:5:

( i ) SEQUENCE CHARACTERISTICS:
        ( A ) LENGTH: 300 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: AMINO TERMINAL PORTION OF XR1PRIM2
        ( VERHT5 . SEQ )

( i x ) FEATURE:
        ( A ) NAME/KEY: CDS
        ( B ) LOCATION: 103..300

( x i ) SEQUENCE DESCRIPTION: SEQ ID NO:5:

```
GTTTTTTTTT TTTTTTTGGT ACCATAGAGT TGCTCTGAAA ACAGAAGATA GAGGGAGTCT        60

CGGAGCTCGC CATCTCCAGC GATCTCTACA TTGGGAAAAA AC ATG GAG TCA GCT         114
                                              Met Glu Ser Ala
                                                1
```

| CCG | GCA | AGG | GAG | ACC | CCG | CTG | AAC | CAG | GAA | TCC | GCC | GCC | CCC | GAC | CCC | 162 |
|---|---|---|---|---|---|---|---|---|---|---|---|---|---|---|---|---|
| Pro | Ala | Arg | Glu | Thr | Pro | Leu | Asn | Gln | Glu | Ser | Ala | Ala | Pro | Asp | Pro | |
| 5 | | | | 10 | | | | | 15 | | | | | | 20 | |

| GCC | GCC | AGC | GAG | CCA | GGC | AGC | AGC | GGC | GCG | GAC | GCG | GCC | GCC | GGC | TCC | 210 |
|---|---|---|---|---|---|---|---|---|---|---|---|---|---|---|---|---|
| Ala | Ala | Ser | Glu | Pro | Gly | Ser | Ser | Gly | Ala | Asp | Ala | Ala | Ala | Gly | Ser | |
| | | | 25 | | | | | 30 | | | | | | 35 | | |

| CGC | AAG | AGC | GAG | CCG | CCT | GCC | CCG | GTG | CGC | AGA | CAG | AGC | TAT | TCC | AGC | 258 |
|---|---|---|---|---|---|---|---|---|---|---|---|---|---|---|---|---|
| Arg | Lys | Ser | Glu | Pro | Pro | Ala | Pro | Val | Arg | Arg | Gln | Ser | Tyr | Ser | Ser | |
| | | | 40 | | | | | 45 | | | | | 50 | | | |

| ACC | AGC | AGA | GGT | ATC | TCA | GTA | ACG | AAG | AAG | ACA | CAT | ACA | TCT | | | 300 |
|---|---|---|---|---|---|---|---|---|---|---|---|---|---|---|---|---|
| Thr | Ser | Arg | Gly | Ile | Ser | Val | Thr | Lys | Lys | Thr | His | Thr | Ser | | | |
| | | 55 | | | | | 60 | | | | | 65 | | | | |

( 2 ) INFORMATION FOR SEQ ID NO:6:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Glu | Ser | Ala | Pro | Ala | Arg | Glu | Thr | Pro | Leu | Asn | Gln | Glu | Ser | Ala |
|---|---|---|---|---|---|---|---|---|---|---|---|---|---|---|---|
| 1 | | | | 5 | | | | | 10 | | | | | 15 | |

| Ala | Pro | Asp | Pro | Ala | Ala | Ser | Glu | Pro | Gly | Ser | Ser | Gly | Ala | Asp | Ala |
|---|---|---|---|---|---|---|---|---|---|---|---|---|---|---|---|
| | | | 20 | | | | 25 | | | | | 30 | | | |

| Ala | Ala | Gly | Ser | Arg | Lys | Ser | Glu | Pro | Pro | Ala | Pro | Val | Arg | Arg | Gln |
|---|---|---|---|---|---|---|---|---|---|---|---|---|---|---|---|
| | | | 35 | | | | 40 | | | | | 45 | | | |

| Ser | Tyr | Ser | Ser | Thr | Ser | Arg | Gly | Ile | Ser | Val | Thr | Lys | Lys | Thr | His |
|---|---|---|---|---|---|---|---|---|---|---|---|---|---|---|---|
| | 50 | | | | | 55 | | | | | 60 | | | | |

Thr Ser
65

( 2 ) INFORMATION FOR SEQ ID NO:7:

( i ) SEQUENCE CHARACTERISTICS:
        ( A ) LENGTH: 1659 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR2 (XR2.SEG)

( i x ) FEATURE:
        ( A ) NAME/KEY: CDS
        ( B ) LOCATION: 148..1470

( x i ) SEQUENCE DESCRIPTION: SEQ ID NO:7:

```
GATATCCGTG ACATCATTGC CTGAGTCCAC TGCAAAAAGC TGTCCCCAGA GCAGGAGGGC        60

AATGACAGCT CCCAGGGCAC TCATCTTGAC TGCTCTTGCC TGGGGATTTG ACAGTGCCT        120

TGGTAATGAC CAGGGCTCCA GAAAGAG ATG TCC TTG TGG CTG GGG GCC CCT           171
                                Met Ser Leu Trp Leu Gly Ala Pro
                                  1               5

GTG CCT GAC ATT CCT CCT GAC TCT GCG GTG GAG CTG TGG AAG CCA GGC        219
Val Pro Asp Ile Pro Pro Asp Ser Ala Val Glu Leu Trp Lys Pro Gly
     10              15                  20

GCA CAG GAT GCA AGC AGC CAG GCC CAG GGA GGC AGC AGC TGC ATC CTC        267
Ala Gln Asp Ala Ser Ser Gln Ala Gln Gly Gly Ser Ser Cys Ile Leu
 25              30                  35                  40

AGA GAG GAA GCC AGG ATG CCC CAC TCT GCT GGG GGT ACT GCA GAG CCC        315
Arg Glu Glu Ala Arg Met Pro His Ser Ala Gly Gly Thr Ala Glu Pro
                 45                  50                  55

ACA GCC CTG CTC ACC AGG GCA GAG CCC CCT TCA GAA CCC ACA GAG ATC        363
Thr Ala Leu Leu Thr Arg Ala Glu Pro Pro Ser Glu Pro Thr Glu Ile
             60                  65                  70

CGT CCA CAA AAG CGG AAA AAG GGG CCA GCC CCC AAA ATG CTG GGG AAC        411
Arg Pro Gln Lys Arg Lys Lys Gly Pro Ala Pro Lys Met Leu Gly Asn
         75                  80                  85

GAG CTA TGC AGC GTG TGT GGG GAC AAG GCC TCG GGC TTC CAC TAC AAT        459
Glu Leu Cys Ser Val Cys Gly Asp Lys Ala Ser Gly Phe His Tyr Asn
     90                  95                 100

GTT CTG AGC TGC GAG GGC TGC AAG GGA TTC TTC CGC CGC AGC GTC ATC        507
Val Leu Ser Cys Glu Gly Cys Lys Gly Phe Phe Arg Arg Ser Val Ile
105                 110                 115                 120

AAG GGA GCG CAC TAC ATC TGC CAC AGT GGC GGC CAC TGC CCC ATG GAC        555
Lys Gly Ala His Tyr Ile Cys His Ser Gly Gly His Cys Pro Met Asp
                125                 130                 135

ACC TAC ATG CGT CGC AAG TGC CAG GAG TGT CGG CTT CGC AAA TGC CGT        603
Thr Tyr Met Arg Arg Lys Cys Gln Glu Cys Arg Leu Arg Lys Cys Arg
             140                 145                 150

CAG GCT GGC ATG CGG GAG GAG TGT GTC CTG TCA GAA GAA CAG ATC CGC        651
Gln Ala Gly Met Arg Glu Glu Cys Val Leu Ser Glu Glu Gln Ile Arg
         155                 160                 165
```

| | | | | | | | | | | | | | | | | |
|---|---|---|---|---|---|---|---|---|---|---|---|---|---|---|---|---|
| CTG | AAG | AAA | CTG | AAG | CGG | CAA | GAG | GAG | GAA | CAG | GCT | CAT | GCC | ACA | TCC | 699 |
| Leu | Lys 170 | Lys | Leu | Lys | Arg | Gln 175 | Glu | Glu | Glu | Gln | Ala 180 | His | Ala | Thr | Ser | |
| TTG | CCC | CCC | AGG | CGT | TCC | TCA | CCC | CCC | CAA | ATC | CTG | CCC | CAG | CTC | AGC | 747 |
| Leu 185 | Pro | Pro | Arg | Arg | Ser 190 | Ser | Pro | Pro | Gln | Ile 195 | Leu | Pro | Gln | Leu | Ser 200 | |
| CCG | GAA | CAA | CTG | GGC | ATG | ATC | GAG | AAG | CTC | GTC | GCT | GCC | CAG | CAA | CAG | 795 |
| Pro | Glu | Gln | Leu | Gly 205 | Met | Ile | Glu | Lys | Leu 210 | Val | Ala | Ala | Gln | Gln 215 | Gln | |
| TGT | AAC | CGG | CGC | TCC | TTT | TCT | GAC | CGG | CTT | CGA | GTC | ACG | CCT | TGG | CCC | 843 |
| Cys | Asn | Arg 220 | Arg | Ser | Phe | Ser | Asp | Arg 225 | Leu | Arg | Val | Thr | Pro 230 | Trp | Pro | |
| ATG | GCA | CCA | GAT | CCC | CAT | AGC | CGG | GAG | GCC | CGT | CAG | CAG | CGC | TTT | GCC | 891 |
| Met | Ala | Pro 235 | Asp | Pro | His | Ser | Arg 240 | Glu | Ala | Arg | Gln | Gln 245 | Arg | Phe | Ala | |
| CAC | TTC | ACT | GAG | CTG | GCC | ATC | GTC | TCT | GTG | CAG | GAG | ATA | GTT | GAC | TTT | 939 |
| His | Phe | Thr 250 | Glu | Leu | Ala | Ile | Val 255 | Ser | Val | Gln | Glu 260 | Ile | Val | Asp | Phe | |
| GCT | AAA | CAG | CTA | CCC | GGC | TTC | CTG | CAG | CTC | AGC | CGG | GAG | GAC | CAG | ATT | 987 |
| Ala 265 | Lys | Gln | Leu | Pro | Gly 270 | Phe | Leu | Gln | Leu | Ser 275 | Arg | Glu | Asp | Gln | Ile 280 | |
| GCC | CTG | CTG | AAG | ACC | TCT | GCG | ATC | GAG | GTG | ATG | CTT | CTG | GAG | ACA | TCT | 1035 |
| Ala | Leu | Leu | Lys | Thr 285 | Ser | Ala | Ile | Glu | Val 290 | Met | Leu | Leu | Glu | Thr 295 | Ser | |
| CGG | AGG | TAC | AAC | CCT | GGG | AGT | GAG | AGT | ATC | ACC | TTC | CTC | AAG | GAT | TTC | 1083 |
| Arg | Arg | Tyr | Asn 300 | Pro | Gly | Ser | Glu | Ser 305 | Ile | Thr | Phe | Leu | Lys 310 | Asp | Phe | |
| AGT | TAT | AAC | CGG | GAA | GAC | TTT | GCC | AAA | GCA | GGG | CTG | CAA | GTG | GAA | TTC | 1131 |
| Ser | Tyr | Asn 315 | Arg | Glu | Asp | Phe | Ala 320 | Lys | Ala | Gly | Leu | Gln 325 | Val | Glu | Phe | |
| ATC | AAC | CCC | ATC | TTC | GAG | TTC | TCC | AGG | GCC | ATG | AAT | GAG | CTG | CAA | CTC | 1179 |
| Ile | Asn 330 | Pro | Ile | Phe | Glu | Phe 335 | Ser | Arg | Ala | Met | Asn 340 | Glu | Leu | Gln | Leu | |
| AAT | GAT | GCC | GAG | TTT | GCC | TTG | CTC | ATT | GCT | ATC | AGC | ATC | TTC | TCT | GCA | 1227 |
| Asn 345 | Asp | Ala | Glu | Phe | Ala 350 | Leu | Leu | Ile | Ala | Ile 355 | Ser | Ile | Phe | Ser | Ala 360 | |
| GAC | CGG | CCC | AAC | GTG | CAG | GAC | CAG | CTC | CAG | GTG | GAG | AGG | CTG | CAG | CAC | 1275 |
| Asp | Arg | Pro | Asn | Val 365 | Gln | Asp | Gln | Leu | Gln 370 | Val | Glu | Arg | Leu | Gln 375 | His | |
| ACA | TAT | GTG | GAA | GCC | CTG | CAT | GCC | TAC | GTC | TCC | ATC | CAC | CAT | CCC | CAT | 1323 |
| Thr | Tyr | Val | Glu 380 | Ala | Leu | His | Ala | Tyr 385 | Val | Ser | Ile | His | His 390 | Pro | His | |
| GAC | CGA | CTG | ATG | TTC | CCA | CGG | ATG | CTA | ATG | AAA | CTG | GTG | AGC | CTC | CGG | 1371 |
| Asp | Arg | Leu 395 | Met | Phe | Pro | Arg | Met 400 | Leu | Met | Lys | Leu | Val 405 | Ser | Leu | Arg | |
| ACC | CTG | AGC | AGC | GTC | CAC | TCA | GAG | CAA | GTG | TTT | GCA | CTG | CGT | CTG | CAG | 1419 |
| Thr | Leu 410 | Ser | Ser | Val | His | Ser 415 | Glu | Gln | Val | Phe | Ala 420 | Leu | Arg | Leu | Gln | |
| GAC | AAA | AAG | CTC | CCA | CCG | CTG | CTC | TCT | GAG | ATC | TGG | GAT | GTG | CAC | GAA | 1467 |
| Asp | Lys 425 | Lys | Leu | Pro | Pro 430 | Leu | Leu | Ser | Glu | Ile 435 | Trp | Asp | Val | His | Glu 440 | |
| TGACTGTTCT | | GTCCCATAT | | TTTCTGTTTT | | CTTGGCCGGA | | TGGCTGAGGC | | CTGGTGGCTG | | | | | | 1527 |
| CCTCCTAGAA | | GTGGAACAGA | | CTGAGAAGGG | | CAAACATTCC | | TGGGAGCTGG | | GCAAGGAGAT | | | | | | 1587 |
| CCTCCCGTGG | | CATTAAAAGA | | GAGTCAAAGG | | GTAAAAAAAA | | AAAAAAAAAA | | AAAAAAAAA | | | | | | 1647 |
| AAAAAGGAAT | | TC | | | | | | | | | | | | | | 1659 |

( 2 ) INFORMATION FOR SEQ ID NO:8:

( i ) SEQUENCE CHARACTERISTICS:
   ( A ) LENGTH: 440 amino acids
   ( B ) TYPE: amino acid
   ( D ) TOPOLOGY: linear ( i i ) MOLECULE TYPE: protein ( x i ) SEQUENCE DESCRIPTION: SEQ ID NO:8:

| Met | Ser | Leu | Trp | Leu | Gly | Ala | Pro | Val | Pro | Asp | Ile | Pro | Pro | Asp | Ser |
|---|---|---|---|---|---|---|---|---|---|---|---|---|---|---|---|
| 1 | | | | 5 | | | | | 10 | | | | | 15 | |
| Ala | Val | Glu | Leu | Trp | Lys | Pro | Gly | Ala | Gln | Asp | Ala | Ser | Ser | Gln | Ala |
| | | | 20 | | | | | 25 | | | | | 30 | | |
| Gln | Gly | Gly | Ser | Ser | Cys | Ile | Leu | Arg | Glu | Glu | Ala | Arg | Met | Pro | His |
| | | 35 | | | | | 40 | | | | | 45 | | | |
| Ser | Ala | Gly | Gly | Thr | Ala | Glu | Pro | Thr | Ala | Leu | Leu | Thr | Arg | Ala | Glu |
| | 50 | | | | | 55 | | | | | 60 | | | | |
| Pro | Pro | Ser | Glu | Pro | Thr | Glu | Ile | Arg | Pro | Gln | Lys | Arg | Lys | Lys | Gly |
| 65 | | | | | 70 | | | | | 75 | | | | | 80 |
| Pro | Ala | Pro | Lys | Met | Leu | Gly | Asn | Glu | Leu | Cys | Ser | Val | Cys | Gly | Asp |
| | | | | 85 | | | | | 90 | | | | | 95 | |
| Lys | Ala | Ser | Gly | Phe | His | Tyr | Asn | Val | Leu | Ser | Cys | Glu | Gly | Cys | Lys |
| | | | 100 | | | | | 105 | | | | | 110 | | |
| Gly | Phe | Phe | Arg | Arg | Ser | Val | Ile | Lys | Gly | Ala | His | Tyr | Ile | Cys | His |
| | | 115 | | | | | 120 | | | | | 125 | | | |
| Ser | Gly | Gly | His | Cys | Pro | Met | Asp | Thr | Tyr | Met | Arg | Arg | Lys | Cys | Gln |
| | 130 | | | | | 135 | | | | | 140 | | | | |
| Glu | Cys | Arg | Leu | Arg | Lys | Cys | Arg | Gln | Ala | Gly | Met | Arg | Glu | Glu | Cys |
| 145 | | | | | 150 | | | | | 155 | | | | | 160 |
| Val | Leu | Ser | Glu | Glu | Gln | Ile | Arg | Leu | Lys | Lys | Leu | Lys | Arg | Gln | Glu |
| | | | | 165 | | | | | 170 | | | | | 175 | |
| Glu | Glu | Gln | Ala | His | Ala | Thr | Ser | Leu | Pro | Pro | Arg | Arg | Ser | Ser | Pro |
| | | | 180 | | | | | 185 | | | | | 190 | | |
| Pro | Gln | Ile | Leu | Pro | Gln | Leu | Ser | Pro | Glu | Gln | Leu | Gly | Met | Ile | Glu |
| | | 195 | | | | | 200 | | | | | 205 | | | |
| Lys | Leu | Val | Ala | Ala | Gln | Gln | Gln | Cys | Asn | Arg | Arg | Ser | Phe | Ser | Asp |
| | 210 | | | | | 215 | | | | | 220 | | | | |
| Arg | Leu | Arg | Val | Thr | Pro | Trp | Pro | Met | Ala | Pro | Asp | Pro | His | Ser | Arg |
| 225 | | | | | 230 | | | | | 235 | | | | | 240 |
| Glu | Ala | Arg | Gln | Gln | Arg | Phe | Ala | His | Phe | Thr | Glu | Leu | Ala | Ile | Val |
| | | | | 245 | | | | | 250 | | | | | 255 | |
| Ser | Val | Gln | Glu | Ile | Val | Asp | Phe | Ala | Lys | Gln | Leu | Pro | Gly | Phe | Leu |
| | | | 260 | | | | | 265 | | | | | 270 | | |
| Gln | Leu | Ser | Arg | Glu | Asp | Gln | Ile | Ala | Leu | Leu | Lys | Thr | Ser | Ala | Ile |
| | | 275 | | | | | 280 | | | | | 285 | | | |
| Glu | Val | Met | Leu | Leu | Glu | Thr | Ser | Arg | Arg | Tyr | Asn | Pro | Gly | Ser | Glu |
| | 290 | | | | | 295 | | | | | 300 | | | | |
| Ser | Ile | Thr | Phe | Leu | Lys | Asp | Phe | Ser | Tyr | Asn | Arg | Glu | Asp | Phe | Ala |
| 305 | | | | | 310 | | | | | 315 | | | | | 320 |
| Lys | Ala | Gly | Leu | Gln | Val | Glu | Phe | Ile | Asn | Pro | Ile | Phe | Glu | Phe | Ser |
| | | | | 325 | | | | | 330 | | | | | 335 | |
| Arg | Ala | Met | Asn | Glu | Leu | Gln | Leu | Asn | Asp | Ala | Glu | Phe | Ala | Leu | Leu |
| | | | 340 | | | | | 345 | | | | | 350 | | |
| Ile | Ala | Ile | Ser | Ile | Phe | Ser | Ala | Asp | Arg | Pro | Asn | Val | Gln | Asp | Gln |
| | | 355 | | | | | 360 | | | | | 365 | | | |
| Leu | Gln | Val | Glu | Arg | Leu | Gln | His | Thr | Tyr | Val | Glu | Ala | Leu | His | Ala |
| | 370 | | | | | 375 | | | | | 380 | | | | |

| | | | | | | | | | | | | | | |
|---|---|---|---|---|---|---|---|---|---|---|---|---|---|---|
| Tyr | Val | Ser | Ile | His | His | Pro | His | Asp | Arg | Leu | Met | Phe | Pro | Arg | Met |
| 385 | | | | | 390 | | | | | 395 | | | | | 400 |

| Leu | Met | Lys | Leu | Val | Ser | Leu | Arg | Thr | Leu | Ser | Ser | Val | His | Ser | Glu |
|---|---|---|---|---|---|---|---|---|---|---|---|---|---|---|---|
| | | | | 405 | | | | | 410 | | | | | 415 | |

| Gln | Val | Phe | Ala | Leu | Arg | Leu | Gln | Asp | Lys | Lys | Leu | Pro | Pro | Leu | Leu |
|---|---|---|---|---|---|---|---|---|---|---|---|---|---|---|---|
| | | | 420 | | | | | 425 | | | | | 430 | | |

| Ser | Glu | Ile | Trp | Asp | Val | His | Glu |
|---|---|---|---|---|---|---|---|
| | | 435 | | | | | 440 |

(2) INFORMATION FOR SEQ ID NO:9:

(i) SEQUENCE CHARACTERISTICS:
        (A) LENGTH: 2009 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: XR4 (XR4.SEG)

(ix) FEATURE:
        (A) NAME/KEY: CDS
        (B) LOCATION: 263..1582

(xi) SEQUENCE DESCRIPTION: SEQ ID NO:9:

```
GAATTCCCTG GGGATTAATG GGAAAAGTTT TGGCAGGAGC TGGGGGATTC TGCGGAGCCT        60

GCGGGACGGC GGCAGCGGCG CGAGAGGCGG CCGGGACAGT GCTGTGCAGC GGTGTGGGTA       120

TGCGCATGGG ACTCACTCAG AGGCTCCTGC TCACTGACAG ATGAAGACAA ACCCACGGTA       180

AAGGCAGTCC ATCTGCGCTC AGACCCAGAT GGTGGCAGAG CTATGACCAG GCCTGCAGCG       240

CCACGCCAAG TGGGGGTCAG TC ATG GAA CAG CCA CAG GAG GAG ACC CCT GAG       292
                         Met Glu Gln Pro Gln Glu Glu Thr Pro Glu
                           1               5                  10
```

| GCC | CGG | GAA | GAG | GAG | AAA | GAG | GAA | GTG | GCC | ATG | GGT | GAC | GGA | GCC | CCG | 340 |
|---|---|---|---|---|---|---|---|---|---|---|---|---|---|---|---|---|
| Ala | Arg | Glu | Glu | Glu | Lys | Glu | Glu | Val | Ala | Met | Gly | Asp | Gly | Ala | Pro | |
| | | | | 15 | | | | 20 | | | | | 25 | | | |

| GAG | CTC | AAT | GGG | GGA | CCA | GAA | CAC | ACG | CTT | CCT | TCC | AGC | AGC | TGT | GCA | 388 |
|---|---|---|---|---|---|---|---|---|---|---|---|---|---|---|---|---|
| Glu | Leu | Asn | Gly | Gly | Pro | Glu | His | Thr | Leu | Pro | Ser | Ser | Ser | Cys | Ala | |
| | | | 30 | | | | | 35 | | | | | 40 | | | |

| GAC | CTC | TCC | CAG | AAT | TCC | TCC | CCT | TCC | TCC | CTG | CTG | GAC | CAG | CTG | CAG | 436 |
|---|---|---|---|---|---|---|---|---|---|---|---|---|---|---|---|---|
| Asp | Leu | Ser | Gln | Asn | Ser | Ser | Pro | Ser | Ser | Leu | Leu | Asp | Gln | Leu | Gln | |
| | | | 45 | | | | | 50 | | | | | 55 | | | |

| ATG | GGC | TGT | GAT | GGG | GCC | TCA | GGC | GGC | AGC | CTC | AAC | ATG | GAA | TGT | CGG | 484 |
|---|---|---|---|---|---|---|---|---|---|---|---|---|---|---|---|---|
| Met | Gly | Cys | Asp | Gly | Ala | Ser | Gly | Gly | Ser | Leu | Asn | Met | Glu | Cys | Arg | |
| | 60 | | | | | 65 | | | | | 70 | | | | | |

| GTG | TGC | GGG | GAC | AAG | GCC | TCG | GGC | TTC | CAC | TAC | GGG | GTC | CAC | GCG | TGC | 532 |
|---|---|---|---|---|---|---|---|---|---|---|---|---|---|---|---|---|
| Val | Cys | Gly | Asp | Lys | Ala | Ser | Gly | Phe | His | Tyr | Gly | Val | His | Ala | Cys | |
| 75 | | | | | 80 | | | | | 85 | | | | | 90 | |

| GAG | GGG | TGC | AAG | GGC | TTC | TTC | CGC | CGG | ACA | ATC | CGC | ATG | AAG | CTC | GAG | 580 |
|---|---|---|---|---|---|---|---|---|---|---|---|---|---|---|---|---|
| Glu | Gly | Cys | Lys | Gly | Phe | Phe | Arg | Arg | Thr | Ile | Arg | Met | Lys | Leu | Glu | |
| | | | | 95 | | | | | 100 | | | | | 105 | | |

| TAT | GAG | AAG | TGC | GAT | CGG | ATC | TGC | AAG | ATC | CAG | AAG | AAG | AAC | CGC | AAC | 628 |
|---|---|---|---|---|---|---|---|---|---|---|---|---|---|---|---|---|
| Tyr | Glu | Lys | Cys | Asp | Arg | Ile | Cys | Lys | Ile | Gln | Lys | Lys | Asn | Arg | Asn | |
| | | | 110 | | | | | 115 | | | | | 120 | | | |

| AAG | TGT | CAG | TAC | TGC | CGC | TTC | CAG | AAG | TGC | CTG | GCA | CTC | GGC | ATG | TCG | 676 |
|---|---|---|---|---|---|---|---|---|---|---|---|---|---|---|---|---|
| Lys | Cys | Gln | Tyr | Cys | Arg | Phe | Gln | Lys | Cys | Leu | Ala | Leu | Gly | Met | Ser | |
| | | 125 | | | | | 130 | | | | | 135 | | | | |

| CAC | AAC | GCT | ATC | CGC | TTT | GGA | CGG | ATG | CCG | GAC | GGC | GAG | AAG | AGG | AAG | 724 |
|---|---|---|---|---|---|---|---|---|---|---|---|---|---|---|---|---|
| His | Asn | Ala | Ile | Arg | Phe | Gly | Arg | Met | Pro | Asp | Gly | Glu | Lys | Arg | Lys | |
| | | 140 | | | | | 145 | | | | | 150 | | | | |

| | | | | | | | | | | | | | | | | |
|---|---|---|---|---|---|---|---|---|---|---|---|---|---|---|---|---|
| CTG | GTG | GCG | GGG | CTG | ACT | GCC | AGC | GAG | GGG | TGC | CAG | CAC | AAC | CCC | CAG | 772 |
| Leu | Val | Ala | Gly | Leu | Thr | Ala | Ser | Glu | Gly | Cys | Gln | His | Asn | Pro | Gln | |
| 155 | | | | 160 | | | | | 165 | | | | | 170 | | |
| CTG | GCC | GAC | CTG | AAG | GCC | TTC | TCT | AAG | CAC | ATC | TAC | AAC | GCC | TAC | CTG | 820 |
| Leu | Ala | Asp | Leu | Lys | Ala | Phe | Ser | Lys | His | Ile | Tyr | Asn | Ala | Tyr | Leu | |
| | | | | 175 | | | | | 180 | | | | | 185 | | |
| AAA | AAC | TTC | AAC | ATG | ACC | AAA | AAG | AAG | GCC | CGG | AGC | ATC | CTC | ACC | GGC | 868 |
| Lys | Asn | Phe | Asn | Met | Thr | Lys | Lys | Lys | Ala | Arg | Ser | Ile | Leu | Thr | Gly | |
| | | | 190 | | | | | 195 | | | | | 200 | | | |
| AAG | TCC | AGC | CAC | AAC | GCA | CCC | TTT | GTC | ATC | CAC | GAC | ATC | GAG | ACA | CTG | 916 |
| Lys | Ser | Ser | His | Asn | Ala | Pro | Phe | Val | Ile | His | Asp | Ile | Glu | Thr | Leu | |
| | | 205 | | | | 210 | | | | | 215 | | | | | |
| TGG | CAG | GCA | GAG | AAG | GGC | CTG | GTG | TGG | AAA | CAG | CTG | GTG | AAC | GTG | CCG | 964 |
| Trp | Gln | Ala | Glu | Lys | Gly | Leu | Val | Trp | Lys | Gln | Leu | Val | Asn | Val | Pro | |
| | 220 | | | | 225 | | | | | 230 | | | | | | |
| CCC | TAC | AAC | GAG | ATC | AGT | GTG | CAC | GTG | TTC | TAC | CGC | TGC | CAG | TCC | ACC | 1012 |
| Pro | Tyr | Asn | Glu | Ile | Ser | Val | His | Val | Phe | Tyr | Arg | Cys | Gln | Ser | Thr | |
| 235 | | | | | 240 | | | | | 245 | | | | | 250 | |
| ACA | GTG | GAG | ACA | GTC | CGA | GAG | CTC | ACC | GAG | TTC | GCC | AAG | AAC | ATC | CCC | 1060 |
| Thr | Val | Glu | Thr | Val | Arg | Glu | Leu | Thr | Glu | Phe | Ala | Lys | Asn | Ile | Pro | |
| | | | | 255 | | | | | 260 | | | | | 265 | | |
| AAC | TTC | AGC | AGC | CTC | TTC | CTC | AAT | GAC | CAG | GTG | ACC | CTC | CTC | AAG | TAT | 1108 |
| Asn | Phe | Ser | Ser | Leu | Phe | Leu | Asn | Asp | Gln | Val | Thr | Leu | Leu | Lys | Tyr | |
| | | | 270 | | | | | 275 | | | | | 280 | | | |
| GGC | GTG | CAC | GAG | GCC | ATC | TTT | GCC | ATG | CTG | GCC | TCC | ATC | GTC | AAC | AAA | 1156 |
| Gly | Val | His | Glu | Ala | Ile | Phe | Ala | Met | Leu | Ala | Ser | Ile | Val | Asn | Lys | |
| | | 285 | | | | 290 | | | | | 295 | | | | | |
| GAC | GGG | CTG | CTG | GTG | GCC | AAC | GGC | AGT | GGC | TTC | GTC | ACC | CAC | GAG | TTC | 1204 |
| Asp | Gly | Leu | Leu | Val | Ala | Asn | Gly | Ser | Gly | Phe | Val | Thr | His | Glu | Phe | |
| | 300 | | | | | 305 | | | | | 310 | | | | | |
| TTG | CGA | AGT | CTC | CGC | AAG | CCC | TTC | AGT | GAC | ATC | ATT | GAG | CCC | AAG | TTC | 1252 |
| Leu | Arg | Ser | Leu | Arg | Lys | Pro | Phe | Ser | Asp | Ile | Ile | Glu | Pro | Lys | Phe | |
| 315 | | | | | 320 | | | | | 325 | | | | | 330 | |
| GAG | TTT | GCT | GTC | AAG | TTC | AAT | GCG | CTG | GAG | CTC | GAT | GAC | AGT | GAC | CTG | 1300 |
| Glu | Phe | Ala | Val | Lys | Phe | Asn | Ala | Leu | Glu | Leu | Asp | Asp | Ser | Asp | Leu | |
| | | | | 335 | | | | | 340 | | | | | 345 | | |
| GCG | CTC | TTC | ATC | GCG | GCC | ATC | ATT | CTG | TGT | GGA | GAC | CGG | CCA | GGC | CTC | 1348 |
| Ala | Leu | Phe | Ile | Ala | Ala | Ile | Ile | Leu | Cys | Gly | Asp | Arg | Pro | Gly | Leu | |
| | | | 350 | | | | | 355 | | | | | 360 | | | |
| ATG | AAT | GTG | CCC | CAG | GTA | GAA | GCC | ATC | CAG | GAC | ACC | ATT | CTG | CGG | GCT | 1396 |
| Met | Asn | Val | Pro | Gln | Val | Glu | Ala | Ile | Gln | Asp | Thr | Ile | Leu | Arg | Ala | |
| | | 365 | | | | 370 | | | | | 375 | | | | | |
| CTA | GAA | TTC | CAT | CTG | CAG | GTC | AAC | CAC | CCT | GAC | AGC | CAG | TAC | CTC | TTC | 1444 |
| Leu | Glu | Phe | His | Leu | Gln | Val | Asn | His | Pro | Asp | Ser | Gln | Tyr | Leu | Phe | |
| | 380 | | | | 385 | | | | | 390 | | | | | | |
| CCC | AAG | CTG | CTG | CAG | AAG | ATG | GCA | GAC | CTG | CGG | CAC | GTG | GTC | ACT | GAG | 1492 |
| Pro | Lys | Leu | Leu | Gln | Lys | Met | Ala | Asp | Leu | Arg | His | Val | Val | Thr | Glu | |
| 395 | | | | 400 | | | | | 405 | | | | | 410 | | |
| CAT | GCC | CAG | ATG | ATG | CAG | TGG | CTA | AAG | AAG | ACG | GAG | AGT | GAG | ACC | TTG | 1540 |
| His | Ala | Gln | Met | Met | Gln | Trp | Leu | Lys | Lys | Thr | Glu | Ser | Glu | Thr | Leu | |
| | | | | 415 | | | | 420 | | | | | 425 | | | |
| CTG | CAC | CCC | CTG | CTC | CAG | GAA | ATC | TAC | AAG | GAC | ATG | TAC | TAAGGCCGCA | | | 1589 |
| Leu | His | Pro | Leu | Leu | Gln | Glu | Ile | Tyr | Lys | Asp | Met | Tyr | | | | |
| | | | 430 | | | | | 435 | | | | 440 | | | | |

```
GCCCAGGCCT CCCCTCAGGC TCTGCTGGGC CCAGCACGG  ACTGTTCAGA GGACCAGCCA    1649

CAGGCACTGG CAGTCAAGCA GCTAGAGCCT ACTCACAACA CTCCAGACAC GTGGCCCAGA    1709

CTCTTCCCCC AACACCCCCA CCCCCACCAA CCCCCCCATT CCCCCAACCC CCCTCCCCCA    1769

CCCCGCTCTC CCCATGGCCC GTTTCCTGTT TCTCCTCAGC ACCTCCTGTT CTTGCTGTCT    1829
```

```
CCCTAGCGCC CTTGCTCCCC CCCCTTTGCC TTCCTTCTCT AGCATCCCCC TCCTCCCAGT    1889
CCTCACATTT GTCTGATTCA CAGCAGACAG CCCGTTGGTA CGCTCACCAG CAGCCTAAAA    1949
GCAGTGGGCC TGTGCTGGCC CAGTCCTGCC TCTCCTCTCT ATCCCCTTCA AAGGGAATTC    2009
```

( 2 ) INFORMATION FOR SEQ ID NO:10:

( i ) SEQUENCE CHARACTERISTICS:
        ( A ) LENGTH: 439 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Glu Gln Pro Gln Glu Glu Thr Pro Glu Ala Arg Glu Glu Lys
 1               5                  10                  15

Glu Glu Val Ala Met Gly Asp Gly Ala Pro Glu Leu Asn Gly Gly Pro
            20                  25                  30

Glu His Thr Leu Pro Ser Ser Ser Cys Ala Asp Leu Ser Gln Asn Ser
        35                  40                  45

Ser Pro Ser Ser Leu Leu Asp Gln Leu Gln Met Gly Cys Asp Gly Ala
    50                  55                  60

Ser Gly Gly Ser Leu Asn Met Glu Cys Arg Val Cys Gly Asp Lys Ala
65                  70                  75                  80

Ser Gly Phe His Tyr Gly Val His Ala Cys Glu Gly Cys Lys Gly Phe
            85                  90                  95

Phe Arg Arg Thr Ile Arg Met Lys Leu Glu Tyr Glu Lys Cys Asp Arg
            100                 105                 110

Ile Cys Lys Ile Gln Lys Lys Asn Arg Asn Lys Cys Gln Tyr Cys Arg
        115                 120                 125

Phe Gln Lys Cys Leu Ala Leu Gly Met Ser His Asn Ala Ile Arg Phe
    130                 135                 140

Gly Arg Met Pro Asp Gly Glu Lys Arg Lys Leu Val Ala Gly Leu Thr
145                 150                 155                 160

Ala Ser Glu Gly Cys Gln His Asn Pro Gln Leu Ala Asp Leu Lys Ala
            165                 170                 175

Phe Ser Lys His Ile Tyr Asn Ala Tyr Leu Lys Asn Phe Asn Met Thr
            180                 185                 190

Lys Lys Lys Ala Arg Ser Ile Leu Thr Gly Lys Ser Ser His Asn Ala
        195                 200                 205

Pro Phe Val Ile His Asp Ile Glu Thr Leu Trp Gln Ala Glu Lys Gly
    210                 215                 220

Leu Val Trp Lys Gln Leu Val Asn Val Pro Pro Tyr Asn Glu Ile Ser
225                 230                 235                 240

Val His Val Phe Tyr Arg Cys Gln Ser Thr Thr Val Glu Thr Val Arg
            245                 250                 255

Glu Leu Thr Glu Phe Ala Lys Asn Ile Pro Asn Phe Ser Ser Leu Phe
            260                 265                 270

Leu Asn Asp Gln Val Thr Leu Leu Lys Tyr Gly Val His Glu Ala Ile
        275                 280                 285

Phe Ala Met Leu Ala Ser Ile Val Asn Lys Asp Gly Leu Leu Val Ala
    290                 295                 300

Asn Gly Ser Gly Phe Val Thr His Glu Phe Leu Arg Ser Leu Arg Lys
305                 310                 315                 320

Pro Phe Ser Asp Ile Ile Glu Pro Lys Phe Glu Phe Ala Val Lys Phe
```

|       |       |       |       | 325   |       |       |       | 330   |       |       |       | 335   |       |       |
| ----- | ----- | ----- | ----- | ----- | ----- | ----- | ----- | ----- | ----- | ----- | ----- | ----- | ----- | ----- |
| Asn   | Ala   | Leu   | Glu   | Leu   | Asp   | Asp   | Ser   | Asp   | Leu   | Ala   | Leu   | Phe   | Ile   | Ala   | Ala   |

```
Asn Ala Leu Glu Leu Asp Asp Ser Asp Leu Ala Leu Phe Ile Ala Ala
                325                 330                 335
Ile Ile Leu Cys Gly Asp Arg Pro Gly Leu Met Asn Val Pro Gln Val
        340                 345                 350
Glu Ala Ile Gln Asp Thr Ile Leu Arg Ala Leu Glu Phe His Leu Gln
    355                 360                 365
Val Asn His Pro Asp Ser Gln Tyr Leu Phe Pro Lys Leu Leu Gln Lys
370                 375                 380
Met Ala Asp Leu Arg His Val Val Thr Glu His Ala Gln Met Met Gln
385                 390                 395                 400
Trp Leu Lys Lys Thr Glu Ser Glu Thr Leu Leu His Pro Leu Leu Gln
        405                 410                 415
Glu Ile Tyr Lys Asp Met Tyr
                420                 425                 430
            435
```

( 2 ) INFORMATION FOR SEQ ID NO:11:

( i ) SEQUENCE CHARACTERISTICS:
        ( A ) LENGTH: 2468 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR5 (XR5.SEG)

( i x ) FEATURE:
        ( A ) NAME/KEY: CDS
        ( B ) LOCATION: 1..1677

( x i ) SEQUENCE DESCRIPTION: SEQ ID NO:11:

```
GAA TTC CGG CGC GGA GGG GCG CGG CGC GAG GGG CCG GAG CCG GGC GGC      48
Glu Phe Arg Arg Gly Gly Ala Arg Arg Glu Gly Pro Glu Pro Gly Gly
  1               5                  10                  15

TCA GGG GCC CAG AGA GTG CGG CGG CCG AGA GCC TGC CGG CCC CTG ACA      96
Ser Gly Ala Gln Arg Val Arg Arg Pro Arg Ala Cys Arg Pro Leu Thr
             20                  25                  30

GCC CCC TCC CCC CGT GGA AGA CCA GGA CGA CGA CTA CGA AGG CGC AAG     144
Ala Pro Ser Pro Arg Gly Arg Pro Gly Arg Arg Leu Arg Arg Arg Lys
         35                  40                  45

TCA TGG CGG AGC AGC GAA CGC CGA GAG GGC CCT GAG CAC CGC CGC ATG     192
Ser Trp Arg Ser Ser Glu Arg Arg Glu Gly Pro Glu His Arg Arg Met
     50                  55                  60

GAG CGG GAC GAA CGG CCA CCT AGC GGA GGG GGA GGC GGC GGG GGC TCG     240
Glu Arg Asp Glu Arg Pro Pro Ser Gly Gly Gly Gly Gly Gly Gly Ser
 65                  70                  75                  80

GCG GGG TTC CTG GAG CCG CCC GCC GCG CTC CCT CCG CCG CCG CGC AAC     288
Ala Gly Phe Leu Glu Pro Pro Ala Ala Leu Pro Pro Pro Pro Arg Asn
                 85                  90                  95

GGT TTC TGT CAG GAT GAA TTG GCA GAG CTT GAT CCA GGC ACT AAT GGA     336
Gly Phe Cys Gln Asp Glu Leu Ala Glu Leu Asp Pro Gly Thr Asn Gly
            100                 105                 110

GAG ACT GAC AGT TTA ACA CTT GGC CAA GGC CAT ATA CCT GTT TCC GTC     384
Glu Thr Asp Ser Leu Thr Leu Gly Gln Gly His Ile Pro Val Ser Val
        115                 120                 125

CCA GAT GAT CGA GCT GAA CAA CGA ACC TGT CTC ATC TGT GGG GAC CGC     432
Pro Asp Asp Arg Ala Glu Gln Arg Thr Cys Leu Ile Cys Gly Asp Arg
    130                 135                 140

GCT ACG GGC TTG CAC TAT GGG ATC ATC TCC TGC GAG GGC TGC AAG GGG     480
```

| | | | | | | | | | | | | | | | | |
|---|---|---|---|---|---|---|---|---|---|---|---|---|---|---|---|---|
| Ala | Thr | Gly | Leu | His | Tyr | Gly | Ile | Ile | Ser | Cys | Glu | Gly | Cys | Lys | Gly | |
| 145 | | | | | 150 | | | | | 155 | | | | | 160 | |
| TTT | TTC | AAG | AGG | AGC | ATT | TGC | AAC | AAA | CGG | GTG | TAT | CGG | TGC | AGT | CGT | 528 |
| Phe | Phe | Lys | Arg | Ser | Ile | Cys | Asn | Lys | Arg | Val | Tyr | Arg | Cys | Ser | Arg | |
| | | | | 165 | | | | | 170 | | | | | 175 | | |
| GAC | AAG | AAC | TGT | GTC | ATG | TCC | CGG | AAG | CAG | AGG | AAC | AGA | TGT | CAG | TAC | 576 |
| Asp | Lys | Asn | Cys | Val | Met | Ser | Arg | Lys | Gln | Arg | Asn | Arg | Cys | Gln | Tyr | |
| | | | 180 | | | | | 185 | | | | | 190 | | | |
| TGC | CGC | CTG | CTC | AAG | TGT | CTC | CAG | ATG | GGC | ATG | AAC | AGG | AAG | GCT | ATC | 624 |
| Cys | Arg | Leu | Leu | Lys | Cys | Leu | Gln | Met | Gly | Met | Asn | Arg | Lys | Ala | Ile | |
| | | 195 | | | | | 200 | | | | | 205 | | | | |
| AGA | GAA | GAT | GGC | ATG | CCT | GGA | GGC | CGG | AAC | AAG | AGC | ATT | GGA | CCA | GTC | 672 |
| Arg | Glu | Asp | Gly | Met | Pro | Gly | Gly | Arg | Asn | Lys | Ser | Ile | Gly | Pro | Val | |
| | 210 | | | | | 215 | | | | | 220 | | | | | |
| CAG | ATA | TCA | GAA | GAA | GAA | ATT | GAA | AGA | ATC | ATG | TCT | GGA | CAG | GAG | TTT | 720 |
| Gln | Ile | Ser | Glu | Glu | Glu | Ile | Glu | Arg | Ile | Met | Ser | Gly | Gln | Glu | Phe | |
| 225 | | | | | 230 | | | | | 235 | | | | | 240 | |
| GAG | GAA | GAA | GCC | AAT | CAC | TGG | AGC | AAC | CAT | GGT | GAC | AGC | GAC | CAC | AGT | 768 |
| Glu | Glu | Glu | Ala | Asn | His | Trp | Ser | Asn | His | Gly | Asp | Ser | Asp | His | Ser | |
| | | | | 245 | | | | | 250 | | | | | 255 | | |
| TCC | CCT | GGG | AAC | AGG | GCT | TCA | GAG | AGC | AAC | CAG | CCC | TCA | CCA | GGC | TCC | 816 |
| Ser | Pro | Gly | Asn | Arg | Ala | Ser | Glu | Ser | Asn | Gln | Pro | Ser | Pro | Gly | Ser | |
| | | | 260 | | | | | 265 | | | | | 270 | | | |
| ACA | CTA | TCA | TCC | AGT | AGG | TCT | GTG | GAA | CTA | AAT | GGA | TTC | ATG | GCA | TTC | 864 |
| Thr | Leu | Ser | Ser | Ser | Arg | Ser | Val | Glu | Leu | Asn | Gly | Phe | Met | Ala | Phe | |
| | | 275 | | | | | 280 | | | | | 285 | | | | |
| AGG | GAT | CAG | TAC | ATG | GGG | ATG | TCA | GTG | CCT | CCA | CAT | TAT | CAA | TAC | ATA | 912 |
| Arg | Asp | Gln | Tyr | Met | Gly | Met | Ser | Val | Pro | Pro | His | Tyr | Gln | Tyr | Ile | |
| | 290 | | | | | 295 | | | | | 300 | | | | | |
| CCA | CAC | CTT | TTT | AGC | TAT | TCT | GGC | CAC | TCA | CCA | CTT | TTG | CCC | CCA | CAA | 960 |
| Pro | His | Leu | Phe | Ser | Tyr | Ser | Gly | His | Ser | Pro | Leu | Leu | Pro | Pro | Gln | |
| 305 | | | | | 310 | | | | | 315 | | | | | 320 | |
| GCT | CGA | AGC | CTG | GAC | CCT | CAG | TCC | TAC | AGT | CTG | ATT | CAT | CAG | CTG | ATG | 1008 |
| Ala | Arg | Ser | Leu | Asp | Pro | Gln | Ser | Tyr | Ser | Leu | Ile | His | Gln | Leu | Met | |
| | | | | 325 | | | | | 330 | | | | | 335 | | |
| TCA | GCC | GAA | GAC | CTG | GAG | CCA | TTG | GGC | ACA | CCT | ATG | TTG | ATT | GAA | GAT | 1056 |
| Ser | Ala | Glu | Asp | Leu | Glu | Pro | Leu | Gly | Thr | Pro | Met | Leu | Ile | Glu | Asp | |
| | | | 340 | | | | | 345 | | | | | 350 | | | |
| GGG | TAT | GCT | GTG | ACA | CAG | GCA | GAA | CTG | TTT | GCT | CTG | CTT | TGC | CGC | CTG | 1104 |
| Gly | Tyr | Ala | Val | Thr | Gln | Ala | Glu | Leu | Phe | Ala | Leu | Leu | Cys | Arg | Leu | |
| | | 355 | | | | | 360 | | | | | 365 | | | | |
| GCC | GAC | GAG | TTG | CTC | TTT | AGG | CAG | ATT | GCC | TGG | ATC | AAG | AAG | CTG | CCT | 1152 |
| Ala | Asp | Glu | Leu | Leu | Phe | Arg | Gln | Ile | Ala | Trp | Ile | Lys | Lys | Leu | Pro | |
| | 370 | | | | | 375 | | | | | 380 | | | | | |
| TTC | TTC | TGC | GAG | CTC | TCA | ATC | AAG | GAT | TAC | ACG | TGC | CTC | TTG | AGC | TCT | 1200 |
| Phe | Phe | Cys | Glu | Leu | Ser | Ile | Lys | Asp | Tyr | Thr | Cys | Leu | Leu | Ser | Ser | |
| 385 | | | | | 390 | | | | | 395 | | | | | 400 | |
| ACG | TGG | CAG | GAG | TTA | ATC | CTG | CTC | TCC | TCC | CTC | ACA | GTG | TAC | AGC | AAG | 1248 |
| Thr | Trp | Gln | Glu | Leu | Ile | Leu | Leu | Ser | Ser | Leu | Thr | Val | Tyr | Ser | Lys | |
| | | | | 405 | | | | | 410 | | | | | 415 | | |
| CAG | ATC | TTT | GGG | GAG | CTG | GCT | GAT | GTC | ACA | GCC | AAG | TAC | TCA | CCC | TCT | 1296 |
| Gln | Ile | Phe | Gly | Glu | Leu | Ala | Asp | Val | Thr | Ala | Lys | Tyr | Ser | Pro | Ser | |
| | | | 420 | | | | | 425 | | | | | 430 | | | |
| GAT | GAA | GAA | CTC | CAC | AGA | TTT | AGT | GAT | GAA | GGG | ATG | GAG | GTG | ATT | GAA | 1344 |
| Asp | Glu | Glu | Leu | His | Arg | Phe | Ser | Asp | Glu | Gly | Met | Glu | Val | Ile | Glu | |
| | | | 435 | | | | | 440 | | | | | 445 | | | |
| CGA | CTC | ATC | TAC | CTA | TAT | CAC | AAG | TTC | CAT | CAG | CTG | AAG | GTC | AGC | AAC | 1392 |
| Arg | Leu | Ile | Tyr | Leu | Tyr | His | Lys | Phe | His | Gln | Leu | Lys | Val | Ser | Asn | |
| | 450 | | | | | 455 | | | | | 460 | | | | | |
| GAG | GAG | TAC | GCA | TGC | ATG | AAA | GCA | ATT | AAC | TTC | CTG | AAT | CAA | GAT | ATC | 1440 |

| | | | | | | | | | | | | | | | | |
|---|---|---|---|---|---|---|---|---|---|---|---|---|---|---|---|---|
| Glu | Glu | Tyr | Ala | Cys | Met | Lys | Ala | Ile | Asn | Phe | Leu | Asn | Gln | Asp | Ile | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| AGG | GGT | CTG | ACC | AGT | GCC | TCA | CAG | CTG | GAA | CAA | CTG | AAC | AAG | CGG | TAT | 1488 |
| Arg | Gly | Leu | Thr | Ser | Ala | Ser | Gln | Leu | Glu | Gln | Leu | Asn | Lys | Arg | Tyr | |
| | | | | 485 | | | | | 490 | | | | | 495 | | |
| TGG | TAC | ATT | TGT | CAG | GAT | TTC | ACT | GAA | TAT | AAA | TAC | ACA | CAT | CAG | CCA | 1536 |
| Trp | Tyr | Ile | Cys | Gln | Asp | Phe | Thr | Glu | Tyr | Lys | Tyr | Thr | His | Gln | Pro | |
| | | | 500 | | | | | 505 | | | | | 510 | | | |
| AAC | CGC | TTT | CCT | GAT | CTT | ATG | ATG | TGC | TTG | CCA | GAG | ATC | CGA | TAC | ATC | 1584 |
| Asn | Arg | Phe | Pro | Asp | Leu | Met | Met | Cys | Leu | Pro | Glu | Ile | Arg | Tyr | Ile | |
| | | 515 | | | | | 520 | | | | | 525 | | | | |
| GCA | GGC | AAG | ATG | GTG | AAT | GTG | CCC | CTG | GAG | CAG | CTG | CCC | CTC | CTC | TTT | 1632 |
| Ala | Gly | Lys | Met | Val | Asn | Val | Pro | Leu | Glu | Gln | Leu | Pro | Leu | Leu | Phe | |
| | | 530 | | | | 535 | | | | | 540 | | | | | |
| AAG | GTG | GTG | CTG | CAC | TCC | TGC | AAG | ACA | AGT | ACG | GTG | AAG | GAG | TGACCTGTGC | | 1684 |
| Lys | Val | Val | Leu | His | Ser | Cys | Lys | Thr | Ser | Thr | Val | Lys | Glu | | | |
| 545 | | | | | 550 | | | | | 555 | | | | | | |

| | | | | | |
|---|---|---|---|---|---|
| CCTGCACCTC | CTTGGGCCAC | CCACAGTGCC | TTGGGTAGGC | AGCACAGGCT | CCAGAGGAAA | 1744 |
| GAGCCAGAGA | CCAAGATGGA | GACTGTGGAG | CAGCTACCTC | CATCACAAGA | AGAATTTGTT | 1804 |
| TGTTTGTCTG | TTTTTAACCT | CATTTTTCTA | TATATTTATT | TCACGACAGA | GTTGAATGTA | 1864 |
| TGGCCTTCAA | CATGATGCAC | ATGCTTTTGT | GTGAATGCAG | CAGATGCATT | TCCTTGCAGT | 1924 |
| TTACAGAATG | TGAAGATGTT | TAATGTTACC | GTGTTGTCAT | TGTTTAGAGA | TAGGTTTTTT | 1984 |
| TGTATTTTGA | TGGAGAGGGT | AGGATGGACT | AGATGAGTAT | TTCCATAATG | TTGACAAAGA | 2044 |
| CAACTACCTC | AATGGAAACA | GGTGTATGAC | CATCCCTACC | TTTTTCCACA | TTTTCTCAGC | 2104 |
| AGATACACAC | TTGTCTGTTA | GAGAGCAAAC | TGCCTTTTTT | ATAGCACAG | ACTTCTAAGT | 2164 |
| AAAAGAAGCA | AACAAAGGAG | CGAAGTGGTA | TAGGGAGATT | TACTAATGGC | CAGTTGGGAC | 2224 |
| ATCTGAGAGG | CAATTTGATT | TTGATCATCT | CATCCCACAA | GCCTGAAGGC | AGAAACTCTG | 2284 |
| CCTTACCTTC | TGCTGCACCC | CTCCCCCCCC | CCACACGCTG | TTGTCTGTTG | ATGCTGCTGT | 2344 |
| CAAGTTTTCA | TCCAGGTAGA | GTCCTAACAA | TAAGCCAGTA | TGTAGGACTT | GCCTCCCAGC | 2404 |
| GCCCTTGTAG | CTCATAGCTG | CCTAGTTTGC | TGTTCTAGAT | CTACCAAGGC | CTACTTCGGA | 2464 |
| ATTC | | | | | | 2468 |

(2) INFORMATION FOR SEQ ID NO:12:

(i) SEQUENCE CHARACTERISTICS:
  (A) LENGTH: 558 amino acids
  (B) TYPE: amino acid
  (D) TOPOLOGY: linear (ii) MOLECULE TYPE: protein (xi) SEQUENCE DESCRIPTION: SEQ ID NO:12:

| | | | | | | | | | | | | | | | |
|---|---|---|---|---|---|---|---|---|---|---|---|---|---|---|---|
| Glu | Phe | Arg | Arg | Gly | Gly | Ala | Arg | Arg | Glu | Gly | Pro | Glu | Pro | Gly | Gly |
| 1 | | | | 5 | | | | | 10 | | | | | 15 | |
| Ser | Gly | Ala | Gln | Arg | Val | Arg | Arg | Pro | Arg | Ala | Cys | Arg | Pro | Leu | Thr |
| | | | 20 | | | | | 25 | | | | | 30 | | |
| Ala | Pro | Ser | Pro | Arg | Gly | Arg | Pro | Gly | Arg | Arg | Leu | Arg | Arg | Arg | Lys |
| | | | 35 | | | | | 40 | | | | | 45 | | |
| Ser | Trp | Arg | Ser | Ser | Glu | Arg | Glu | Gly | Pro | Glu | His | Arg | Arg | Met | |
| | | 50 | | | | | 55 | | | | | 60 | | | |
| Glu | Arg | Asp | Glu | Arg | Pro | Pro | Ser | Gly | Gly | Gly | Gly | Gly | Gly | Ser | |
| 65 | | | | | 70 | | | | | 75 | | | | | 80 |
| Ala | Gly | Phe | Leu | Glu | Pro | Pro | Ala | Ala | Leu | Pro | Pro | Pro | Pro | Arg | Asn |
| | | | | 85 | | | | | 90 | | | | | 95 | |

```
Gly Phe Cys Gln Asp Glu Leu Ala Glu Leu Asp Pro Gly Thr Asn Gly
            100                 105                 110
Glu Thr Asp Ser Leu Thr Leu Gly Gln Gly His Ile Pro Val Ser Val
        115                 120                 125
Pro Asp Asp Arg Ala Glu Gln Arg Thr Cys Leu Ile Cys Gly Asp Arg
    130                 135                 140
Ala Thr Gly Leu His Tyr Gly Ile Ile Ser Cys Glu Gly Cys Lys Gly
145                 150                 155                 160
Phe Phe Lys Arg Ser Ile Cys Asn Lys Arg Val Tyr Arg Cys Ser Arg
                165                 170                 175
Asp Lys Asn Cys Val Met Ser Arg Lys Gln Arg Asn Arg Cys Gln Tyr
            180                 185                 190
Cys Arg Leu Leu Lys Cys Leu Gln Met Gly Met Asn Arg Lys Ala Ile
        195                 200                 205
Arg Glu Asp Gly Met Pro Gly Gly Arg Asn Lys Ser Ile Gly Pro Val
    210                 215                 220
Gln Ile Ser Glu Glu Glu Ile Glu Arg Ile Met Ser Gly Gln Glu Phe
225                 230                 235                 240
Glu Glu Glu Ala Asn His Trp Ser Asn His Gly Asp Ser Asp His Ser
                245                 250                 255
Ser Pro Gly Asn Arg Ala Ser Glu Ser Asn Gln Pro Ser Pro Gly Ser
            260                 265                 270
Thr Leu Ser Ser Ser Arg Ser Val Glu Leu Asn Gly Phe Met Ala Phe
        275                 280                 285
Arg Asp Gln Tyr Met Gly Met Ser Val Pro Pro His Tyr Gln Tyr Ile
    290                 295                 300
Pro His Leu Phe Ser Tyr Ser Gly His Ser Pro Leu Leu Pro Pro Gln
305                 310                 315                 320
Ala Arg Ser Leu Asp Pro Gln Ser Tyr Ser Leu Ile His Gln Leu Met
                325                 330                 335
Ser Ala Glu Asp Leu Glu Pro Leu Gly Thr Pro Met Leu Ile Glu Asp
            340                 345                 350
Gly Tyr Ala Val Thr Gln Ala Glu Leu Phe Ala Leu Leu Cys Arg Leu
        355                 360                 365
Ala Asp Glu Leu Leu Phe Arg Gln Ile Ala Trp Ile Lys Lys Leu Pro
    370                 375                 380
Phe Phe Cys Glu Leu Ser Ile Lys Asp Tyr Thr Cys Leu Leu Ser Ser
385                 390                 395                 400
Thr Trp Gln Glu Leu Ile Leu Leu Ser Ser Leu Thr Val Tyr Ser Lys
                405                 410                 415
Gln Ile Phe Gly Glu Leu Ala Asp Val Thr Ala Lys Tyr Ser Pro Ser
            420                 425                 430
Asp Glu Glu Leu His Arg Phe Ser Asp Glu Gly Met Glu Val Ile Glu
        435                 440                 445
Arg Leu Ile Tyr Leu Tyr His Lys Phe His Gln Leu Lys Val Ser Asn
    450                 455                 460
Glu Glu Tyr Ala Cys Met Lys Ala Ile Asn Phe Leu Asn Gln Asp Ile
465                 470                 475                 480
Arg Gly Leu Thr Ser Ala Ser Gln Leu Glu Gln Leu Asn Lys Arg Tyr
                485                 490                 495
Trp Tyr Ile Cys Gln Asp Phe Thr Glu Tyr Lys Tyr Thr His Gln Pro
            500                 505                 510
Asn Arg Phe Pro Asp Leu Met Met Cys Leu Pro Glu Ile Arg Tyr Ile
```

5,571,696

47 48

-continued

|  |  |  | 515 |  |  |  | 520 |  |  |  | 525 |  |  |  |
|---|---|---|---|---|---|---|---|---|---|---|---|---|---|---|
| Ala | Gly | Lys | Met | Val | Asn | Val | Pro | Leu | Glu | Gln | Leu | Pro | Leu | Leu | Phe |
|  |  | 530 |  |  |  | 535 |  |  |  | 540 |  |  |  |
| Lys | Val | Val | Leu | His | Ser | Cys | Lys | Thr | Ser | Thr | Val | Lys | Glu |
| 545 |  |  |  |  | 550 |  |  |  |  | 555 |  |  |  |

( 2 ) INFORMATION FOR SEQ ID NO:13:

( i ) SEQUENCE CHARACTERISTICS:
        ( A ) LENGTH: 2315 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: XR79 (XR79.SEQ)

( i x ) FEATURE:
        ( A ) NAME/KEY: CDS
        ( B ) LOCATION: 204..2009

( x i ) SEQUENCE DESCRIPTION: SEQ ID NO:13:

```
GCGTTAGAAA  AGGTTCAAAA  TAGGCACAAA  GTCGTGAAAA  TATCGTAACT  GACCGGAAGT         60

AACATAACTT  TAACCAAGTG  CCTCGAAAAA  TAGATGTTTT  TAAAAGCTCA  AGAATGGTGA        120

TAACAGACGT  CCAATAAGAA  TTTTCAAAGA  GCCAATTATT  TATACAGCCG  ACGACTATTT        180

TTTAGCCGCC  TGCTGTGGCG  ACA ATG GAC GGC GTT AAG GTT GAG ACG TTC              230
                          Met Asp Gly Val Lys Val Glu Thr Phe
                           1               5

ATC AAA AGC GAA GAA AAC CGA GCG ATG CCC TTG ATC GGA GGA GGC AGT             278
Ile Lys Ser Glu Glu Asn Arg Ala Met Pro Leu Ile Gly Gly Gly Ser
 10              15                  20                  25

GCC TCA GGC GGC ACT CCT CTG CCA GGA GGC GGC GTG GGA ATG GGA GCC             326
Ala Ser Gly Gly Thr Pro Leu Pro Gly Gly Gly Val Gly Met Gly Ala
                 30                  35                  40

GGA GCA TCC GCA ACG TTG AGC GTG GAG CTG TGT TTG GTG TGC GGG GAC             374
Gly Ala Ser Ala Thr Leu Ser Val Glu Leu Cys Leu Val Cys Gly Asp
                 45                  50                  55

CGC GCC TCC GGG CGG CAC TAC GGA GCC ATA AGC TGC GAA GGC TGC AAG             422
Arg Ala Ser Gly Arg His Tyr Gly Ala Ile Ser Cys Glu Gly Cys Lys
             60                  65                  70

GGA TTC TTC AAG CGC TCG ATC CGG AAG CAG CTG GGC TAC CAG TGT CGC             470
Gly Phe Phe Lys Arg Ser Ile Arg Lys Gln Leu Gly Tyr Gln Cys Arg
 75                  80                  85

GGG GCT ATG AAC TGC GAG GTC ACC AAG CAC CAC AGG AAT CGG TGC CAG             518
Gly Ala Met Asn Cys Glu Val Thr Lys His His Arg Asn Arg Cys Gln
 90                  95                 100                 105

TTC TGT CGA CTA CAG AAG TGC CTG GCC AGC GGC ATG CGA AGT GAT TCT             566
Phe Cys Arg Leu Gln Lys Cys Leu Ala Ser Gly Met Arg Ser Asp Ser
                110                 115                 120

GTG CAG CAC GAG AGG AAA CCG ATT GTG GAC AGG AAG GAG GGG ATC ATC             614
Val Gln His Glu Arg Lys Pro Ile Val Asp Arg Lys Glu Gly Ile Ile
             125                 130                 135

GCT GCT GCC GGT AGC TCA TCC ACT TCT GGC GGC GGT AAT GGC TCG TCC             662
Ala Ala Ala Gly Ser Ser Ser Thr Ser Gly Gly Gly Asn Gly Ser Ser
         140                 145                 150

ACC TAC CTA TCC GGC AAG TCC GGC TAT CAG CAG GGG CGT GGC AAG GGG             710
Thr Tyr Leu Ser Gly Lys Ser Gly Tyr Gln Gln Gly Arg Gly Lys Gly
         155                 160                 165

CAC AGT GTA AAG GCC GAA TCC GCG CCA CGC CTC CAG TGC ACA GCG CGC             758
His Ser Val Lys Ala Glu Ser Ala Pro Arg Leu Gln Cys Thr Ala Arg
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 170 |     |     |     |     | 175 |     |     |     |     | 180 |     |     |     |     | 185 |      |
| CAG | CAA | CGG | GCC | TTC | AAT | TTG | AAT | GCA | GAA | TAT | ATT | CCG | ATG | GGT | TTG | 806  |
| Gln | Gln | Arg | Ala | Phe | Asn | Leu | Asn | Ala | Glu | Tyr | Ile | Pro | Met | Gly | Leu |      |
|     |     |     |     | 190 |     |     |     |     | 195 |     |     |     |     | 200 |     |      |
| AAT | TTC | GCA | GAA | CTA | ACG | CAG | ACA | TTG | ATG | TTC | GCT | ACC | CAA | CAG | CAG | 854  |
| Asn | Phe | Ala | Glu | Leu | Thr | Gln | Thr | Leu | Met | Phe | Ala | Thr | Gln | Gln | Gln |      |
|     |     |     | 205 |     |     |     |     | 210 |     |     |     |     | 215 |     |     |      |
| CAG | CAA | CAA | CAG | CAA | CAG | CAT | CAA | CAG | AGT | GGT | AGC | TAT | TCG | CCA | GAT | 902  |
| Gln | Gln | Gln | Gln | Gln | Gln | His | Gln | Gln | Ser | Gly | Ser | Tyr | Ser | Pro | Asp |      |
|     |     | 220 |     |     |     |     | 225 |     |     |     |     | 230 |     |     |     |      |
| ATT | CCG | AAG | GCA | GAT | CCC | GAG | GAT | GAC | GAG | GAC | GAC | TCA | ATG | GAC | AAC | 950  |
| Ile | Pro | Lys | Ala | Asp | Pro | Glu | Asp | Asp | Glu | Asp | Asp | Ser | Met | Asp | Asn |      |
|     | 235 |     |     |     |     | 240 |     |     |     |     | 245 |     |     |     |     |      |
| AGC | AGC | ACG | CTG | TGC | TTG | CAG | TTG | CTC | GCC | AAC | AGC | GCC | AGC | AAC | AAC | 998  |
| Ser | Ser | Thr | Leu | Cys | Leu | Gln | Leu | Leu | Ala | Asn | Ser | Ala | Ser | Asn | Asn |      |
| 250 |     |     |     |     | 255 |     |     |     |     | 260 |     |     |     |     | 265 |      |
| AAC | TCG | CAG | CAC | CTG | AAC | TTT | AAT | GCT | GGG | GAA | GTA | CCC | ACC | GCT | CTG | 1046 |
| Asn | Ser | Gln | His | Leu | Asn | Phe | Asn | Ala | Gly | Glu | Val | Pro | Thr | Ala | Leu |      |
|     |     |     |     | 270 |     |     |     |     | 275 |     |     |     |     | 280 |     |      |
| CCT | ACC | ACC | TCG | ACA | ATG | GGG | CTT | ATT | CAG | AGT | TCG | CTG | GAC | ATG | CGG | 1094 |
| Pro | Thr | Thr | Ser | Thr | Met | Gly | Leu | Ile | Gln | Ser | Ser | Leu | Asp | Met | Arg |      |
|     |     |     | 285 |     |     |     |     | 290 |     |     |     |     | 295 |     |     |      |
| GTC | ATC | CAC | AAG | GGA | CTG | CAG | ATC | CTG | CAG | CCC | ATC | CAA | AAC | CAA | CTG | 1142 |
| Val | Ile | His | Lys | Gly | Leu | Gln | Ile | Leu | Gln | Pro | Ile | Gln | Asn | Gln | Leu |      |
|     |     | 300 |     |     |     |     | 305 |     |     |     |     | 310 |     |     |     |      |
| GAG | CGA | AAT | GGT | AAT | CTG | AGT | GTG | AAG | CCC | GAG | TGC | GAT | TCA | GAG | GCG | 1190 |
| Glu | Arg | Asn | Gly | Asn | Leu | Ser | Val | Lys | Pro | Glu | Cys | Asp | Ser | Glu | Ala |      |
|     | 315 |     |     |     |     | 320 |     |     |     |     | 325 |     |     |     |     |      |
| GAG | GAC | AGT | GGC | ACC | GAG | GAT | GCC | GTA | GAC | GCG | GAG | CTG | GAG | CAC | ATG | 1238 |
| Glu | Asp | Ser | Gly | Thr | Glu | Asp | Ala | Val | Asp | Ala | Glu | Leu | Glu | His | Met |      |
| 330 |     |     |     |     | 335 |     |     |     |     | 340 |     |     |     |     | 345 |      |
| GAA | CTA | GAC | TTT | GAG | TGC | GGT | GGG | AAC | CGA | AGC | GGT | GGA | AGC | GAT | TTT | 1286 |
| Glu | Leu | Asp | Phe | Glu | Cys | Gly | Gly | Asn | Arg | Ser | Gly | Gly | Ser | Asp | Phe |      |
|     |     |     |     | 350 |     |     |     |     | 355 |     |     |     |     | 360 |     |      |
| GCT | ATC | AAT | GAG | GCG | GTC | TTT | GAA | CAG | GAT | CTT | CTC | ACC | GAT | GTG | CAG | 1334 |
| Ala | Ile | Asn | Glu | Ala | Val | Phe | Glu | Gln | Asp | Leu | Leu | Thr | Asp | Val | Gln |      |
|     |     |     | 365 |     |     |     |     | 370 |     |     |     |     | 375 |     |     |      |
| TGT | GCC | TTT | CAT | GTG | CAA | CCG | CCG | ACT | TTG | GTC | CAC | TCG | TAT | TTA | AAT | 1382 |
| Cys | Ala | Phe | His | Val | Gln | Pro | Pro | Thr | Leu | Val | His | Ser | Tyr | Leu | Asn |      |
|     |     | 380 |     |     |     |     | 385 |     |     |     |     | 390 |     |     |     |      |
| ATT | CAT | TAT | GTG | TGT | GAG | ACG | GGC | TCG | CGA | ATC | ATT | TTT | CTC | ACC | ATC | 1430 |
| Ile | His | Tyr | Val | Cys | Glu | Thr | Gly | Ser | Arg | Ile | Ile | Phe | Leu | Thr | Ile |      |
|     | 395 |     |     |     |     | 400 |     |     |     |     | 405 |     |     |     |     |      |
| CAT | ACC | CTT | CGA | AAG | GTT | CCA | GTT | TTC | GAA | CAA | TTG | GAA | GCC | CAT | ACA | 1478 |
| His | Thr | Leu | Arg | Lys | Val | Pro | Val | Phe | Glu | Gln | Leu | Glu | Ala | His | Thr |      |
| 410 |     |     |     |     | 415 |     |     |     |     | 420 |     |     |     |     | 425 |      |
| CAG | GTG | AAA | CTC | CTG | AGA | GGA | GTG | TGG | CCA | GCA | TTA | ATG | GCT | ATA | GCT | 1526 |
| Gln | Val | Lys | Leu | Leu | Arg | Gly | Val | Trp | Pro | Ala | Leu | Met | Ala | Ile | Ala |      |
|     |     |     |     | 430 |     |     |     |     | 435 |     |     |     |     | 440 |     |      |
| TTG | GCG | CAG | TGT | CAG | GGT | CAG | CTT | TCG | GTG | CCC | ACC | ATT | ATC | GGG | CAG | 1574 |
| Leu | Ala | Gln | Cys | Gln | Gly | Gln | Leu | Ser | Val | Pro | Thr | Ile | Ile | Gly | Gln |      |
|     |     |     | 445 |     |     |     |     | 450 |     |     |     |     | 455 |     |     |      |
| TTT | ATT | CAA | AGC | ACT | CGC | CAG | CTA | GCG | GAT | ATC | GAT | AAG | ATC | GAA | CCG | 1622 |
| Phe | Ile | Gln | Ser | Thr | Arg | Gln | Leu | Ala | Asp | Ile | Asp | Lys | Ile | Glu | Pro |      |
|     |     | 460 |     |     |     |     | 465 |     |     |     |     | 470 |     |     |     |      |
| TTG | AAG | ATC | TCG | AAG | ATG | GCA | AAT | CTC | ACC | AGG | ACC | CTG | CAC | GAC | TTT | 1670 |
| Leu | Lys | Ile | Ser | Lys | Met | Ala | Asn | Leu | Thr | Arg | Thr | Leu | His | Asp | Phe |      |
|     | 475 |     |     |     |     | 480 |     |     |     |     | 485 |     |     |     |     |      |
| GTC | CAG | GAG | CTC | CAG | TCA | CTG | GAT | GTT | ACT | GAT | ATG | GAG | TTT | GGC | TTG | 1718 |
| Val | Gln | Glu | Leu | Gln | Ser | Leu | Asp | Val | Thr | Asp | Met | Glu | Phe | Gly | Leu |      |

| | | | | | | | | | | | | | | | | |
|---|---|---|---|---|---|---|---|---|---|---|---|---|---|---|---|---|
|490| | | | |495| | | | |500| | | | |505| |
|CTG|CGT|CTG|ATC|TTG|CTC|TTC|AAT|CCA|ACG|CTC|TTC|CAG|CAT|CGC|AAG|1766|
|Leu|Arg|Leu|Ile|Leu|Leu|Phe|Asn|Pro|Thr|Leu|Phe|Gln|His|Arg|Lys| |
| | | |510| | | | |515| | | | |520| | | |
|GAG|CGG|TCG|TTG|CGA|GGC|TAC|GTC|CGC|AGA|GTC|CAA|CTC|TAC|GCT|CTG|1814|
|Glu|Arg|Ser|Leu|Arg|Gly|Tyr|Val|Arg|Arg|Val|Gln|Leu|Tyr|Ala|Leu| |
| | |525| | | | |530| | | | |535| | | | |
|TCA|AGT|TTG|AGA|AGG|CAG|GGT|GGC|ATC|GGC|GGC|GGC|GAG|GAG|CGC|TTT|1862|
|Ser|Ser|Leu|Arg|Arg|Gln|Gly|Gly|Ile|Gly|Gly|Gly|Glu|Glu|Arg|Phe| |
| | |540| | | | |545| | | | |550| | | | |
|AAT|GTT|CTG|GTG|GCT|CGC|CTT|CTT|CCG|CTC|AGC|AGC|CTG|GAC|GCA|GAG|1910|
|Asn|Val|Leu|Val|Ala|Arg|Leu|Leu|Pro|Leu|Ser|Ser|Leu|Asp|Ala|Glu| |
| |555| | | | |560| | | | |565| | | | | |
|GCC|ATG|GAG|GAG|CTG|TTC|TTC|GCC|AAC|TTG|GTG|GGG|CAG|ATG|CAG|ATG|1958|
|Ala|Met|Glu|Glu|Leu|Phe|Phe|Ala|Asn|Leu|Val|Gly|Gln|Met|Gln|Met| |
|570| | | | |575| | | | |580| | | | |585| |
|GAT|GCT|CTT|ATT|CCG|TTC|ATA|CTG|ATG|ACC|AGC|AAC|ACC|AGT|GGA|CTG|2006|
|Asp|Ala|Leu|Ile|Pro|Phe|Ile|Leu|Met|Thr|Ser|Asn|Thr|Ser|Gly|Leu| |
| | | |590| | | | |595| | | | |600| | | |

| | | | | | |
|---|---|---|---|---|---|
|TAGGCGGAAT|TGAGAAGAAC|AGGGCGCAAG|CAGATTCGCT|AGACTGCCCA|AAAGCAAGAC|2066|
|TGAAGATGGA|CCAAGTGCGG|GCAATACATG|TAGCAACTAG|GCAAATCCCA|TTAATTATAT|2126|
|ATTTAATATA|TACAATATAT|AGTTTAGGAT|ACAATATTCT|AACATAAAAC|CATGAGTTTA|2186|
|TTGTTGTTCA|CAGATAAAAT|GGAATCGATT|TCCCAATAAA|AGCGAATATG|TTTTTAAACA|2246|
|GAATGTTTGC|ATCAGAACTT|TGAGATGTAT|ACATTAGATT|ATTACAACAC|AAAAAAAAAA|2306|
|AAAAAAAA| | | | | |2315|

( 2 ) INFORMATION FOR SEQ ID NO:14:

( i ) SEQUENCE CHARACTERISTICS:
        ( A ) LENGTH: 601 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | | |
|---|---|---|---|---|---|---|---|---|---|---|---|---|---|---|---|
|Met|Asp|Gly|Val|Lys|Val|Glu|Thr|Phe|Ile|Lys|Ser|Glu|Glu|Asn|Arg|
|1| | | |5| | | | |10| | | | |15| |
|Ala|Met|Pro|Leu|Ile|Gly|Gly|Gly|Ser|Ala|Ser|Gly|Gly|Thr|Pro|Leu|
| | | |20| | | | |25| | | | |30| | |
|Pro|Gly|Gly|Gly|Val|Gly|Met|Gly|Ala|Gly|Ala|Ser|Ala|Thr|Leu|Ser|
| | |35| | | | |40| | | | |45| | | |
|Val|Glu|Leu|Cys|Leu|Val|Cys|Gly|Asp|Arg|Ala|Ser|Gly|Arg|His|Tyr|
| |50| | | | |55| | | | |60| | | | |
|Gly|Ala|Ile|Ser|Cys|Glu|Gly|Cys|Lys|Gly|Phe|Phe|Lys|Arg|Ser|Ile|
|65| | | | |70| | | | |75| | | | |80|
|Arg|Lys|Gln|Leu|Gly|Tyr|Gln|Cys|Arg|Gly|Ala|Met|Asn|Cys|Glu|Val|
| | | | |85| | | | |90| | | | |95| |
|Thr|Lys|His|His|Arg|Asn|Arg|Cys|Gln|Phe|Cys|Arg|Leu|Gln|Lys|Cys|
| | | |100| | | | |105| | | | |110| | |
|Leu|Ala|Ser|Gly|Met|Arg|Ser|Asp|Ser|Val|Gln|His|Glu|Arg|Lys|Pro|
| | |115| | | | |120| | | | |125| | | |
|Ile|Val|Asp|Arg|Lys|Glu|Gly|Ile|Ile|Ala|Ala|Ala|Gly|Ser|Ser|Ser|
| |130| | | | |135| | | | |140| | | | |
|Thr|Ser|Gly|Gly|Gly|Asn|Gly|Ser|Ser|Thr|Tyr|Leu|Ser|Gly|Lys|Ser|
|145| | | | |150| | | | |155| | | | |160|

```
Gly  Tyr  Gln  Gln  Gly  Arg  Gly  Lys  Gly  His  Ser  Val  Lys  Ala  Glu  Ser
               165                      170                      175

Ala  Pro  Arg  Leu  Gln  Cys  Thr  Ala  Arg  Gln  Gln  Arg  Ala  Phe  Asn  Leu
               180                      185                      190

Asn  Ala  Glu  Tyr  Ile  Pro  Met  Gly  Leu  Asn  Phe  Ala  Glu  Leu  Thr  Gln
               195                      200                      205

Thr  Leu  Met  Phe  Ala  Thr  Gln  Gln  Gln  Gln  Gln  Gln  Gln  Gln  Gln  His
          210                      215                      220

Gln  Gln  Ser  Gly  Ser  Tyr  Ser  Pro  Asp  Ile  Pro  Lys  Ala  Asp  Pro  Glu
225                      230                      235                      240

Asp  Asp  Glu  Asp  Asp  Ser  Met  Asp  Asn  Ser  Ser  Thr  Leu  Cys  Leu  Gln
               245                      250                      255

Leu  Leu  Ala  Asn  Ser  Ala  Ser  Asn  Asn  Ser  Gln  His  Leu  Asn  Phe
               260                      265                      270

Asn  Ala  Gly  Glu  Val  Pro  Thr  Ala  Leu  Pro  Thr  Thr  Ser  Thr  Met  Gly
               275                      280                      285

Leu  Ile  Gln  Ser  Ser  Leu  Asp  Met  Arg  Val  Ile  His  Lys  Gly  Leu  Gln
          290                      295                      300

Ile  Leu  Gln  Pro  Ile  Gln  Asn  Gln  Leu  Glu  Arg  Asn  Gly  Asn  Leu  Ser
305                      310                      315                      320

Val  Lys  Pro  Glu  Cys  Asp  Ser  Glu  Ala  Glu  Asp  Ser  Gly  Thr  Glu  Asp
               325                      330                      335

Ala  Val  Asp  Ala  Glu  Leu  Glu  His  Met  Glu  Leu  Asp  Phe  Glu  Cys  Gly
               340                      345                      350

Gly  Asn  Arg  Ser  Gly  Gly  Ser  Asp  Phe  Ala  Ile  Asn  Glu  Ala  Val  Phe
               355                      360                      365

Glu  Gln  Asp  Leu  Leu  Thr  Asp  Val  Gln  Cys  Ala  Phe  His  Val  Gln  Pro
370                      375                      380

Pro  Thr  Leu  Val  His  Ser  Tyr  Leu  Asn  Ile  His  Tyr  Val  Cys  Glu  Thr
385                      390                      395                      400

Gly  Ser  Arg  Ile  Ile  Phe  Leu  Thr  Ile  His  Thr  Leu  Arg  Lys  Val  Pro
               405                      410                      415

Val  Phe  Glu  Gln  Leu  Glu  Ala  His  Thr  Gln  Val  Lys  Leu  Leu  Arg  Gly
               420                      425                      430

Val  Trp  Pro  Ala  Leu  Met  Ala  Ile  Ala  Leu  Ala  Gln  Cys  Gln  Gly  Gln
               435                      440                      445

Leu  Ser  Val  Pro  Thr  Ile  Ile  Gly  Gln  Phe  Ile  Gln  Ser  Thr  Arg  Gln
     450                      455                      460

Leu  Ala  Asp  Ile  Asp  Lys  Ile  Glu  Pro  Leu  Lys  Ile  Ser  Lys  Met  Ala
465                      470                      475                      480

Asn  Leu  Thr  Arg  Thr  Leu  His  Asp  Phe  Val  Gln  Glu  Leu  Gln  Ser  Leu
               485                      490                      495

Asp  Val  Thr  Asp  Met  Glu  Phe  Gly  Leu  Leu  Arg  Leu  Ile  Leu  Leu  Phe
               500                      505                      510

Asn  Pro  Thr  Leu  Phe  Gln  His  Arg  Lys  Glu  Arg  Ser  Leu  Arg  Gly  Tyr
               515                      520                      525

Val  Arg  Arg  Val  Gln  Leu  Tyr  Ala  Leu  Ser  Ser  Leu  Arg  Arg  Gln  Gly
     530                      535                      540

Gly  Ile  Gly  Gly  Gly  Glu  Glu  Arg  Phe  Asn  Val  Leu  Val  Ala  Arg  Leu
545                      550                      555                      560

Leu  Pro  Leu  Ser  Ser  Leu  Asp  Ala  Glu  Ala  Met  Glu  Glu  Leu  Phe  Phe
               565                      570                      575

Ala  Asn  Leu  Val  Gly  Gln  Met  Gln  Met  Asp  Ala  Leu  Ile  Pro  Phe  Ile
               580                      585                      590
```

```
Leu  Met  Thr  Ser  Asn  Thr  Ser  Gly  Leu
          595                      600
```

RECEPTORS

This invention was made with Government support under Grant Nos. GM 26444, DK 26741 and HD 27183, awarded by the National Institute of Health. The Government has certain rights in the invention.

This application is a continuation of application Ser. No. 07/761,068, filed Sep. 17, 1991, now abandoned.

FIELD OF THE INVENTION

The present invention relates to novel steroid-hormone or steroid-hormone like receptor proteins, genes encoding such proteins, and methods of making and using such proteins. In a particular aspect, the present invention relates to bioassay systems for determining the selectivity of interaction between ligands and steroid-hormone or steroid-hormone like receptor proteins.

BACKGROUND OF THE INVENTION

Transcriptional regulation of development and homeostasis in complex eukaryotes, including humans and other mammals, birds, fish, insects, and the like, is controlled by a wide variety of regulatory substances, including steroid and thyroid hormones. These hormones exert potent effects on development and differentiation of phylogenetically diverse organisms. The effects of hormones are mediated by interaction with specific, high affinity binding proteins referred to as receptors.

The ability to identify additional compounds which are able to affect transcription of genes which are responsive to steroid hormones or metabolites thereof, would be of significant value in identifying compounds of potential therapeutic use. Further, systems useful for monitoring solutions, body fluids, and the like, for the presence of steroid hormones or metabolites thereof, would be of value in medical diagnosis, as well as for various biochemical applications.

A number of receptor proteins, each specific for one of several classes of cognate steroid hormones [e.g., estrogens (estrogen receptor), progesterones (progesterone receptor), glucocorticoid (glucocorticoid receptor), androgens (androgen receptor), aldosterones (mineralocorticoid receptor), vitamin D (vitamin D receptor)], retinoids (e.g., retinoic acid receptor) or for cognate thyroid hormones (e.g., thyroid hormone receptor), are known. Receptor proteins have been found to be distributed throughout the cell population of complex eukaryotes in a tissue specific fashion.

Molecular cloning studies have made it possible to demonstrate that receptors for steroid, retinoid and thyroid hormones are all structurally related and comprise a superfamily of regulatory proteins. These regulatory proteins are capable of modulating specific gene expression in response to hormone stimulation by binding directly to cis-acting elements. Structural comparisons and functional studies with mutant receptors have revealed that these molecules are composed of a series of discrete functional domains, most notably, a DNA-binding domain that is composed typically of 66–68 amino acids, including two zinc fingers and an associated carboxy terminal stretch of approximately 250 amino acids, which latter region comprises the ligand-binding domain.

An important advance in the characterization of this superfamily of regulatory proteins has been the delineation of a growing list of gene products which possess the structural features of hormone receptors. This growing list of gene products has been isolated by low-stringency hybridization techniques employing DNA sequences encoding previously identified hormone receptor proteins.

It is known that steroid or thyroid hormones, protected forms thereof, or metabolites thereof, enter cells and bind to the corresponding specific receptor protein, initiating an allosteric alteration of the protein. As a result of this alteration, the complex of receptor and hormone (or metabolite thereof) is capable of binding to certain specific sites on chromatin with high affinity.

It is also known that many of the primary effects of steroid and thyroid hormones involve increased transcription of a subset of genes in specific cell types.

A number of steroid hormone- and thyroid hormone-responsive transcriptional control units have been identified. These include the mouse mammary tumor virus 5'-long terminal repeat (MTV LTR), responsive to glucocorticoid, aldosterone and androgen hormones; the transcriptional control units for mammalian growth hormone genes, responsive to glucocorticoids, estrogens and thyroid hormones; the transcriptional control units for mammalian prolactin genes and progesterone receptor genes, responsive to estrogens; the transcriptional control units for avian ovalbumin genes, responsive to progesterones; mammalian metallothionein gene transcriptional control units, responsive to glucocorticoids; and mammalian hepatic $\alpha_{2u}$-gloubulin gene transcriptional control units, responsive to androgens, estrogens, thyroid hormones, and glucocorticoids.

A major obstacle to further understanding and more widespread use of the various members of the steroid/thyroid superfamily of hormone receptors has been a lack of availability of the receptor proteins, in sufficient quantity and sufficiently pure form, to allow them to be adequately characterized. The same is true for the DNA gene segments which encode them. Lack of availability of these DNA segments has prevented in vitro manipulation and in vivo expression of the receptor-encoding genes, and consequently the knowledge such manipulation and expression would yield.

In addition, a further obstacle to a more complete understanding and more widespread use of members of the steroid/thyroid receptor superfamily is the fact that additional members of this superfamily remain to be discovered, isolated and characterized.

The present invention is directed to overcoming these problems of short supply of adequately purified receptor material, lack of DNA segments which encode such receptors and increasing the number of identified and characterized hormone receptors which are available for use.

BRIEF DESCRIPTION OF THE INVENTION

In accordance with the present invention, we have discovered novel members of the steroid/thyroid superfamily of receptors. The novel receptors of the present invention are soluble, intracellular, nuclear (as opposed to cell surface) receptors, which are activated to modulate transcription of certain genes in animal cells when the cells are exposed to ligands therefor. The nuclear receptors of the present invention differ significantly from known steroid receptors, both in primary sequence and in responsiveness to exposure of cells to various ligands, e.g., steroids or steroid-like compounds.

Also provided in accordance with the present invention are DNAs encoding the receptors of the present invention, including expression vectors for expression thereof in animal cells, cells transformed with such expression vectors, cells co-transformed with such expression vectors and reporter vectors (to monitor the ability of the receptors to modulate transcription when the cells are exposed to a compound which interacts with the receptor); and methods of using such co-transformed cells in screening for compounds which are capable of leading to modulation of receptor activity.

Further provided in accordance with the present invention are DNA and RNA probes for identifying DNAs encoding additional steroid receptors.

In accordance with yet another embodiment of the invention, there is provided a method for making the receptors of the invention by expressing DNAs which encode the receptors in suitable host organisms.

The novel receptors and DNAs encoding same can be employed for a variety of purposes. For example, novel receptors of the present invention can be included as part of a panel of receptors which are screened to determine the selectivity of interaction of proposed agonists or antagonists and other receptors. Thus, a compound which is believed to interact selectively, for example, with the glucocorticoid receptor, should not have any substantial effect on any other receptors, including those of the present invention. Conversely, if such a proposed compound does interact with one or more of the invention receptors, then the possibility of side reactions caused by such compound is clearly indicated.

BRIEF DESCRIPTION OF THE FIGURE

FIG. 1 is a schematic diagram correlating the relationship between the alternate spliced variants of invention receptor XR1.

DETAILED DESCRIPTION OF THE INVENTION

In accordance with the present invention, there are provided DNAs encoding a polypeptide characterized by having a DNA binding domain comprising about 66 amino acids with 9 cysteine (Cys) residues, wherein said DNA binding domain has:

(i) less than about 70% amino acid sequence identity with the DNA binding domain of human retinoic acid receptor-alpha (hRAR-alpha);

(ii) less than about 60% amino acid sequence identity with the DNA binding domain of human thyroid receptor-beta (hTR-beta);

(iii) less than about 50% amino acid sequence identity with the DNA binding domain of human glucocorticoid receptor (hGR); and (iv) less than about 65% amino acid sequence identity in with the DNA binding domain of human retinoid X receptor-alpha (hRXR-alpha).

Alternatively, DNAs of the invention can be characterized with respect to percent amino acid sequence identity of the ligand binding domain of polypeptides encoded thereby, relative to amino acid sequences of previously characterized receptors. As yet another alternative, DNAs of the invention can be characterized by the percent overall amino acid sequence identity of polypeptides encoded thereby, relative to amino acid sequences of previously characterized receptors.

Thus, DNAs of the invention can be characterized as encoding polypeptides having, in the ligand binding domain:

(i) less than about 35% amino acid sequence identity with the ligand binding domain of hRAR-alpha;

(ii) less than about 30% amino acid sequence identity with the ligand binding domain of hTR-beta;

(iii) less than about 25% amino acid sequence identity with the ligand binding domain of hGR; and (iv) less than about 30% amino acid sequence identity with the ligand binding domain of hRXR-alpha.

DNAs of the invention can be further characterized as encoding polypeptides having an overall amino acid sequence identity of:

(i) less than about 35% relative to hRAR-alpha;

(ii) less than about 35% relative to hTR-beta;

(iii) less than about 25% relative to hGR; and (iv) less than about 35% relative to hRXR-alpha.

Specific receptors contemplated for use in the practice of the present invention include:

"XR1" (variously referred to herein as receptor "XR1", "hXR1", "hXR1. pep" or "verHT19. pep"; wherein the prefix "h" indicates the clone is of human origin), a polypeptide characterized as having a DNA binding domain comprising:

(i) about 68% amino acid sequence identity with the DNA binding domain of hRAR-alpha;

(ii) about 59% amino acid sequence identity with the DNA binding domain of hTR-beta;

(iii) about 45% amino acid sequence identity with the DNA binding domain of hGR; and (iv) about 65% amino acid sequence identity with the DNA binding domain of hRXR-alpha;

see also Sequence ID No. 2 for a specific amino acid sequence representative of XR1, as well as Sequence ID No. 1 which is an exemplary nucleotide sequence encoding XR1. In addition, Sequence ID Nos. 4 and 6 present alternate amino terminal sequences for the clone referred to as XR1 (the variant referred to as verht3 is presented in Sequence ID No. 4 (an exemplary nucleotide sequence encoding such variant presented in Sequence ID No. 3), and the variant referred to as verhr5 is presented in Sequence ID No. 6 (an exemplary nucleotide sequence encoding such variant presented in Sequence ID No. 5);

"XR2" (variously referred to herein as receptor "XR2", "hXR2" or "hXR2.pep"), a polypeptide characterized as having a DNA binding domain comprising:

(i) about 55% amino acid sequence identity with the DNA binding domain of hRAR-alpha;

(ii) about 56% amino acid sequence identity with the DNA binding domain of hTR-beta;

(iii) about 50% amino acid sequence identity with the DNA binding domain of hGR; and (iv) about 52% amino acid sequence identity with the DNA binding domain of hRXR-alpha; see also Sequence ID No. 8 for a specific amino acid sequence representative of XR2, as well as Sequence ID No. 7 which is an exemplary nucleotide sequence encoding XR2;

"XR4" (variously referred to herein as receptor "XR4", "mXR4" or "mXR4. pep"; wherein the prefix "m" indicates the clone is of mouse origin), a polypeptide characterized as having a DNA binding domain comprising:

(i) about 62% amino acid sequence identity with the DNA binding domain of hRAR-alpha;

(ii) about 58% amino acid sequence identity with the DNA binding domain of hTR-beta;

(iii) about 48% amino acid sequence identity with the DNA binding domain of hGR; and (iv) about 62% amino acid sequence identity with the DNA binding domain of hRXR-alpha;

see also Sequence ID No. 10 for a specific amino acid sequence representative of XR4, as well as Sequence ID No. 9 which is an exemplary nucleotide sequence encoding XR4;

"XR5" (variously referred to herein as receptor "XR5", "mXR5" or "mXR5.pep" ), a polypeptide characterized as having a DNA binding domain comprising:
(i) about 59% amino acid sequence identity with the DNA binding domain of hRAR-alpha;
(ii) about 52% amino acid sequence identity with the DNA binding domain of hTR-beta;
(iii) about 44% amino acid sequence identity with the DNA binding domain of hGR; and
(iv) about 61% amino acid sequence identity with the DNA binding domain of hRXR-alpha;

see also Sequence ID No. 12 for a specific amino acid sequence representative of XR5, as well as Sequence ID No. 11 which is an exemplary nucleotide sequence encoding XR5; and "XR79" (variously referred to herein as "XR79", "dXR79" or "dXR79.pep"; wherein the prefix "d" indicates the clone is of Drosophila origin), a polypeptide characterized as having a DNA binding domain comprising:
(i) about 59% amino acid sequence identity with the DNA binding domain of hRAR-alpha;
(ii) about 55% amino acid sequence identity with the DNA binding domain of hTR-beta;
(iii) about 50% amino acid sequence identity with the DNA binding domain of hGR; and
(iv) about 65% amino acid sequence identity with the DNA binding domain of hRXR-alpha;

see also Sequence ID No. 14 for a specific amino acid sequence representative of XR79, as well as Sequence ID No. 13 which is an exemplary nucleotide sequence encoding XR79.

The receptor referred to herein as "XR1" is observed as three closely related proteins, presumably produced by alternate splicing from a single gene. The first of these proteins to be characterized (referred to herein XR1; also to as "verht19") comprises about 548 amino acids, and has a $M_r$ of about 63 kilodalton. Northern analysis indicates that a single mRNA species corresponding to XR1 is highly expressed in the brain. A variant of XR1 (verht19), herein referred to as "verht3", XR1' or XR1prime, is further characterized as comprising about 556 amino acids, and having a $M_r$ of about 64 kilodalton. Yet another variant of XR1 (verht19), referred to herein as "verhr5", XR1" or XR1prim2, is further characterized as comprising about 523 amino acids, and having a $M_r$ of about 60 kilodalton. The interrelationship between these three variants of XR1 is illustrated schematically in FIG. 1.

The receptor referred to herein as "XR2" is further characterized as a protein comprising about 440 amino acids, and having a $M_r$ of about 50 kilodalton. Northern analysis indicates that a single mRNA species (~1.7 kb) corresponding to XR2 is expressed most highly in liver, kidney, lung, intestine and adrenals of adult male rats. Transactivation studies (employing chimeric receptors containing the XR2 DNA binding domain and the ligand binding domain of a prior art receptor) indicate that XR2 is capable of binding to $TRE_{pal}$. In terms of amino acid sequence identity with prior art receptors, XR2 is most closely related to the vitamin D receptor (39% overall amino acid sequence identity, 17% amino acid identity in the amino terminal domain of the receptor, 53% amino acid identity in the DNA binding domain of the receptor and 37% amino acid identity in the ligand binding domain of the receptor).

The receptor referred to herein as "XR4" is further characterized as a protein comprising about 439 amino acids, and having a $M_r$ of about 50 kilodalton. In terms of amino acid sequence identity with prior art receptors, XR4 is most closely related to the peroxisome proliferator-activated receptor (62% overall amino acid sequence identity, 30% amino acid identity in the amino terminal domain of the receptor, 86% amino acid identity in the DNA binding domain of the receptor and 64% amino acid identity in the ligand binding domain of the receptor). XR4 is expressed ubiquitously and throughout development (as determined by in situ hybridization).

The receptor referred to herein as "XR5" is further characterized as a protein comprising about 556 amino acids, and having a $M_r$ of about 64 kilodalton. In situ hybridization reveals widespread expression throughout development. High levels of expression are observed in the embryonic liver around day 12, indicating a potential role in haematopoiesis. High levels are also found in maturing dorsal root ganglia and in the skin. In terms of amino acid sequence identity with prior art receptors, XR5 is most closely related to the rat nerve growth factor induced protein-B (NGFI-B) receptor. With respect to NGFI-B, XR5 has 29% overall amino acid sequence identity, 15% amino acid identity in the amino terminal domain of the receptor, 52% amino acid identity in the DNA binding domain of the receptor and 29% amino acid identity in the ligand binding domain of the receptor.

The receptor referred to herein as "XR79" is further characterized as a protein comprising about 601 amino acids, and having a $M_r$ of about 66 kilodalton. Whole mount in situ hybridization reveals a fairly uniform pattern of RNA expression during embryogenesis. Northern blot analysis indicates that a 2.5 kb transcript corresponding to XR79 is present in RNA throughout development. The levels of XR79 mRNA are highest in RNA from 0–3 hour old embryos, i.e., maternal product, and lowest in RNA from the second instar larvae (L2 stage). In situ hybridization reveals that XR79 is distributed relatively uniformly at different stages of embryogenesis. In terms of amino acid sequence identity with prior art receptors, XR79 is most closely related to the mammalian receptor TR2 [see Chang and Kokontis in Biochemical and Biophysical Research Communications 155: 971–977 (1988)], as well as members of the coup family, i.e., ear2, coup(ear3), harp-1. With respect to TR2, XR79 has 33% overall amino acid sequence identity, 16% amino acid identity in the amino terminal domain of the receptor, 74% amino acid identity in the DNA binding domain of the receptor and 28% amino acid identity in the ligand binding domain of the receptor. With respect to coup (ear3) [see Miyajima et al., in Nucl Acids Res 16: 11057–11074 (1988)], XR79 has 32% overall amino acid sequence identity, 21% amino acid identity in the amino terminal domain of the receptor, 62% amino acid identity in the DNA binding domain of the receptor and 22% amino acid identity in the ligand binding domain of the receptor.

In accordance with a specific embodiment of the present invention, there is provided an expression vector which comprises DNA as previously described (or functional fragments thereof), and which further comprises:
at the 5'-end of said DNA, a promoter and a nucleotide triplet encoding a translational start codon, and
at the 3'-end of said DNA, a nucleotide triplet encoding a translational stop codon;

wherein said expression vector is operative in a cell in culture (e.g., yeast, bacteria, mammalian) to express the protein encoded by said DNA.

As employed herein, reference to "functional fragments" embraces DNA encoding portions of the invention receptors which retain one or more of the functional characteristics of steroid hormone or steroid hormone-like receptors, e.g., DNA binding properties of such receptors, ligand binding properties of such receptors, the ability to heterodimerize, nuclear localization properties of such receptors, phosphorylation properties of such receptors, transactivation domains characteristic of such receptors, and the like.

In accordance with a further embodiment of the present invention, there are provided cells in culture (e.g., yeast, bacteria, mammalian) which are transformed with the above-described expression vector.

In accordance with yet another embodiment of the present invention, there is provided a method of making the above-described novel receptors (or functional fragments thereof) by culturing the above-described cells under conditions suitable for expression of polypeptide product.

In accordance with a further embodiment of the present invention, there are provided novel polypeptide products produced by the above-described method.

In accordance with a still further embodiment of the present invention, there are provided chimeric receptors comprising at least an amino-terminal domain, a DNA-binding domain, and a ligand-binding domain, wherein at least one of the domains thereof is derived from the novel polypeptides of the present invention; and wherein at least one of the domains thereof is derived from at least one previously identified member of the steroid/thyroid superfamily of receptors e.g., glucocorticoid receptor (GR), thyroid receptors (TR), retinoic acid receptors (RAR), mineralocorticoid receptor (MR), estrogen receptor (ER), the estrogen related receptors (e.g., hERR1 or hERR2), retinoid X receptors (e.g., RXRα, RXRβ or RXRδ), vitamin D receptor (VDR), aldosterone receptor (AR), progesterone receptor (PR), the ultraspiracle receptor (USP), nerve growth factor induced protein-B (NGFI-B), the coup family of transcription factors (COUP), peroxisome proliferator-activated receptor (PPAR), mammalian receptor TR2 (TR2), and the like.

In accordance with yet another embodiment of the present invention, there is provided a method of using polypeptides of the invention to screen for response elements and/or ligands for the novel receptors described herein. The method to identify compounds which act as ligands for receptor polypeptides of the invention comprising:

assaying for the presence or absence of reporter protein upon contacting of cells containing a chimeric form of said receptor polypeptide and reporter vector with said compound;

wherein said chimeric form of said receptor polypeptide comprises the ligand binding domain of said receptor polypeptide and the amino-terminal and DNA-binding domains of one or more previously identified members of the steroid/thyroid superfamily of receptors;

wherein said reporter vector comprises:
(a) a promoter that is operable in said cell,
(b) a hormone response element which is responsive to the receptor from which the DNA-binding domain of said chimeric form of said receptor polypeptide is derived, and
(c) a DNA segment encoding a reporter protein,
wherein said reporter protein-encoding DNA segment is operatively linked to said promoter for transcription of said DNA segment, and
wherein said hormone response element is operatively linked to said promoter for activation thereof, and thereafter identifying those compounds which induce or block the production of reporter in the presence of said chimeric form of said receptor polypeptide.

The method to identify response elements for receptor polypeptides of the invention comprises:

assaying for the presence or absence of reporter protein upon contacting of cells containing a chimeric form of said receptor polypeptide and reporter vector with a compound which is a known agonist or antagonist for the receptor from which the ligand-binding domain of said chimeric form of said receptor polypeptide is derived;

wherein said chimeric form of said receptor polypeptide comprises the DNA-binding domain of the receptor polypeptide and the amino-terminal and ligand-binding domains of one or more previously identified members of the steroid/thyroid superfamily of receptors;

wherein said reporter vector comprises:
(a) a promoter that is operable in said cell,
(b) a putative hormone response element, and
(c) a DNA segment encoding a reporter protein,
wherein said reporter protein-encoding DNA segment is operatively linked to said promoter for transcription of said DNA segment, and
wherein said hormone response element is operatively linked to said promoter for activation thereof; and identifying those response elements for which the production of reporter is induced or blocked in the presence of said chimeric form of said receptor polypeptide.

In accordance with yet another embodiment of the present invention, there is provided a DNA or RNA labeled for detection; wherein said DNA or RNA comprises a nucleic acid segment, preferably of at least 20 bases in length, wherein said segment has substantially the same sequence as a segment of the same length selected from the DNA segment represented by bases 21–1902, inclusive, of Sequence ID No. 1, bases 1–386, inclusive, of Sequence ID No. 3, bases 10–300, inclusive, of Sequence ID No. 5, bases 21–1615, inclusive, of Sequence ID No. 7, bases 21–2000, inclusive, of Sequence ID No. 9, bases 1–2450, inclusive, of Sequence ID No. 11, bases 21–2295, inclusive, of Sequence ID No. 13, or the complement of any of said segments.

In accordance with still another embodiment of the present invention, there are provided methods of testing compound(s) for the ability to regulate transcription-activating effects of a receptor polypeptide, said method comprising assaying for the presence or absence of reporter protein upon contacting of cells containing a receptor polypeptide and reporter vector with said compound;

wherein said receptor polypeptide is characterized by having a DNA binding domain comprising about 66 amino acids with 9 Cys residues, wherein said DNA binding domain has:
(i) less than about 70% amino acid sequence identity with the DNA binding domain of hRAR-alpha;
(ii) less than about 60% amino acid sequence identity with the DNA binding domain of hTR-beta;
(iii) less than about 50% amino acid sequence identity with the DNA binding domain of hGR; and (iv) less than about 65% amino acid sequence identity with the DNA binding domain of hRXR-alpha; and wherein said reporter vector comprises:
(a) a promoter that is operable in said cell,
(b) a hormone response element, and
(c) a DNA segment encoding a reporter protein, wherein said reporter protein-encoding DNA segment is operatively linked to said promoter for transcription of said DNA segment, and wherein said hormone response element is operatively linked to said promoter for activation thereof.

In accordance with a still further embodiment of the present invention, there is provided a method of testing a compound for its ability to selectively regulate the transcription-activating effects of a specific receptor polypeptide, said method comprising:

assaying for the presence or absence of reporter protein upon contacting of cells containing said receptor polypeptide and reporter vector with said compound;

wherein said receptor polypeptide is characterized by being responsive to the presence of a known ligand for said receptor to regulate the transcription of associated gene(s);

wherein said reporter vector comprises:
(a) a promoter that is operable in said cell,
(b) a hormone response element, and
(c) a DNA segment encoding a reporter protein,
    wherein said reporter protein-encoding DNA segment is operatively linked to said promoter for transcription of said DNA segment, and
    wherein said hormone response element is operatively linked to said promoter for activation thereof; and assaying for the presence or absence of reporter protein upon contacting of cells containing chimeric receptor polypeptide and reporter vector with said compound;
    wherein said chimeric receptor polypeptide comprises the ligand binding domain of a novel receptor of the present invention, and the DNA binding domain of said specific receptor; and thereafter selecting those compounds which induce or block the production of reporter in the presence of said specific receptor, but are substantially unable to induce or block the production of reporter in the presence of said chimeric receptor.

The above-described methods of testing compounds for the ability to regulate transcription-activating effects of invention receptor polypeptides can be carried out employing methods described in U.S. Ser. No. 108,471, filed Oct. 20, 1987, issued as U.S. Pat. No. 5,071,773 on Dec. 10, 1991, the entire contents of which are hereby incorporated by reference herein.

As employed herein, the term "expression vector" refers to constructs containing DNA of the invention (or functional fragments thereof), plus all sequences necessary for manipulation and expression of such DNA. Such an expression vector will contain both a "translational start site" and a "translational stop site". Those of skill in the art can readily identify sequences which act as either translational start sites or translational stop sites.

Suitable host cells for use in the practice of the present invention include prokaroytic and eukaryote cells, e.g., bacteria, yeast, mammalian cells and the like.

Labeled DNA or RNA contemplated for use in the practice of the present invention comprises nucleic acid sequences covalently attached to readily analyzable species such as, for example, radiolabel (e.g., $^{32}P$, $^{3}H$, $^{35}S$, and the like), enzymatically active label, and the like.

The invention will now be described in greater detail by reference to the following non-limiting examples.

EXAMPLES

Example I

Isolation and Characterization of XR1

The KpnI/SacI restriction fragment (503bp) including the DNA-binding domain of hRAR-alpha-encoding DNA [See Giguere et al., Nature 330: 624–629 (1987); and commonly assigned U.S. patent application Ser. No. 276,536, filed Nov. 30, 1988; and European Patent Application Publication No. 0 325 849, all incorporated herein by reference] was nick-translated and used to screen a rat brain cDNA library [see DNA Cloning, A practical approach, Vol I and II, D. M. Glover, ed. (IRL Press (1985)] and a lambda-gt11 human liver cDNA library [Kwok et al., Biochem. 24: 556 (1985)] at low stringency. The hybridization mixture contained 35% formamide, 1X Denhardt's, 5X SSPE (1X SSPE=0.15M NaCl, 10 mM $Na_2HPO_4$ 1 mM EDTA), 0.1% SDS, 10% dextran sulfate, 100 µg/ml denatured salmon sperm DNA and $10^6$ cpm of [$^{32}P$]-labelled probe. Duplicate nitrocellulose filters were hybridized for 16 h at 42° C., washed once at 25° C. for 15 min with 2X SSC (1X SSC=0.15M NaCl, 0.015M sodium citrate), 0.1% SDS and then washed twice at 55° C. for 30 min. in 2X SSC, 0.1% SDS. The filters were autoradiographed for 3 days at –70° C. using an intensifying screen.

After several rounds of screening, a pure positive clone having an insert of about 2.1 kb is obtained from the rat brain cDNA library. Several positive clones are obtained from the human liver library. Sequence analysis of the positive rat brain clone indicates that this clone encodes a novel member of the steroid/thyroid superfamily of receptors. Sequence analysis of one of the positive human liver clones (designated "hL1" a 1.7 kb cDNA) indicates that this clone is the human equivalent of the rat brain clone, based on sequence homology.

The EcoRI insert of clone hL1 (labeled with $^{32}P$) is also used as a probe to screen a human testis cDNA library (Clonetech) and a human retina cDNA library [see Nathans et al., in Science 232: 193–202 (1986)]. Hybridization conditions comprised a hybridization mixture containing 50% formamide, 1X Denhardt's, 5X SSPE, 0.1% SDS, 100 µg/ml denatured salmon sperm DNA and $10^6$ cpm of [$^{32}P$]-labelled probe. Duplicate nitrocellulose filters were hybridized for 16 h at 42° C., washed once at 25° C. for 15 min with 2X SSC (1X SSC=0.15M NaCl 0.015M sodium citrate), 0.1% SDS and then washed twice at 55° C. for 30 min. in 2X SSC, 0.1% SDS. The filters were autoradiographed for 3 days at –70° C. using an intensifying screen.

After several rounds of screening, five (5) positive clones were obtained from the human retina cDNA library, and five (5) positive clones were obtained from the human testis cDNA library. Sequence analysis of two clones from the testis library indicates that these clones encode different isoforms of the same novel member of the steroid/thyroid superfamily of receptors (designated as XR1; also referred to herein as "Verht19" and XR1; also referred to herein as "Verht3"). Sequence analysis of one of the positive clones from the human retina library indicates that this clone is yet another isoform of the same novel member of the steroid/thyroid superfamily of receptors (designated XR1"; also referred to herein as "Verhr5"). The full length sequence of (i.e. Verht 19) is set forth herein as Sequence ID No. 1 (which includes an indication of where the splice site is for each of the variants, verht3 and verhr5). The amino-terminal sequence of verht3 and verhr5 are presented in Sequence ID Nos. 3 and 5, respectively. In addition, the interrelationship between each of these three isoforms is illustrated schematically in FIG. 1.

Example II

Isolation and Characterization of XR2

The KpnI/SacI restriction fragment (503 bp) including the DNA-binding domain of hRAR-alpha-encoding DNA [See Giguere et al., Nature 330: 624 (1987); and commonly assigned U.S. patent application Ser. No. 276,536, filed Nov. 30, 1988; and European Patent Application Publication No. 0 325 849, all incorporated herein by reference] was nick-translated and used to screen a lambda-gt11 human liver cDNA library [Kwok et al.,Biochem. 24: 556 (1985)] at low stringency. The hybridization mixture contained 35% formamide, 1X Denhardt's, 5X SSPE (1X SSPE=0.15M NaCl, 10 mM $Na_2HPO_4$ 1 mM EDTA), 0.1% SDS, 10% dextran sulfate, 100 mg/ml denatured salmon sperm DNA and $10^6$ cpm of [$^{32}$P]-labelled probe. Duplicate nitrocellulose filters were hybridized for 16 h at 42° C., washed once at 25° C. for 15 min with 2X SSC (1X SSC=0.15M NaCl, 0.015M sodium citrate), 0.1% SDS and then washed twice at 55° C. for 30 min. in 2X SSC, 0.1% SDS. The filters were autoradiographed for 3 days at −70° C. using an intensifying screen.

Positive clones were isolated, subcloned into pGEM vectors (Promega, Madison, Wis., USA), restriction mapped, and re-subcloned in various sized restriction fragments into M13mp18 and M13mp19 sequencing vectors. DNA sequence was determined by the dideoxy method with Sequenase™ sequencing kit (United States Biochemical, Cleveland, Ohio, USA) and analyzed by University of Wisconsin Genetics Computer Group programs [Devereux et al., *Nucl. Acids Res.* 12, 387 (1984)]. Several clones of a unique receptor-like sequence were identified, the longest of which was designated lambda-HL1-1 (also referred to herein as XR2).

The DNA sequence of the resulting clone is set forth as Sequence ID No. 7.

Example III

Isolation and Characterization of XR4

A clone which encodes a portion of the coding sequence for XR4 was isolated from a mouse embryonic library by screening under low stringency conditions (as described above).

The library used was a lambda gt10 day 8.5 cDNA library having an approximate titer of $1.3×10^{10}$/ml (derived from 8.5 day old embryonic material with as much of the amnion and extraembryonic tissues dissected away as possible). This library was prepared from poly A$^+$selected RNA (by oligo-dT priming), Gubler & Hoffman cloning methods [Gene 25: 263 (1983)], and cloned into the EcoRI site of lambda gt10.

The probe used was a mixture of radioactively labeled DNA derived from the DNA binding regions of the human alpha and beta retinoic acid receptors.

Positive clones were isolated, subcloned into pGEM vectors (Promega, Madison, Wis., USA), restriction mapped, and re-subcloned in various sized restriction fragments into M13mp18 and M13mp19 sequencing vectors. DNA sequence was determined by the dideoxy method with Sequenase™ sequencing kit (United States Biochemical, Cleveland, Ohio, USA) and analyzed by University of Wisconsin Genetics Computer Group programs [Devereux et al., Nucl. Acids Res. 12, 387 (1984)]. Several clones of a unique receptor-like sequence were identified, the longest of which was designated XR4.

The DNA sequence of the resulting clone is set forth as Sequence ID No. 9.

Example IV

Isolation and Characterization of XR5

A clone which encodes a portion of the coding sequence for XR5 was isolated from a mouse embryonic library by screening under low stringency conditions (as described above).

The library used was the same lambda gt10 day 8.5 cDNA library described in the preceding example. Similarly, the probe used was the same mixture of radioactively labeled DNA described in the preceding example.

Only one of the clones isolated corresponds to a portion of the coding region for XR5. A 0.7 kb EcoRI fragment of this clone (designated as No. II-17) was subcloned into the bluescript pksII-Vector. Partial sequence analysis of this insert fragment shows homology to the DNA binding domain of the retinoic acid receptors.

The EcoRI-insert was used to rescreen a second library (a mouse lambda ZAPII day 6.5 cDNA library, prepared as described below) under high stringency conditions. A total of 21 phages were isolated and rescued into the psk-vector. Partial sequencing allowed inserts from 13 of these phages to be identified as having sequences which overlap with XR5 II-17. The clone with the longest single EcoRI-insert was sequenced, revealing an open reading frame of 556 amino acids. This sequence was extended further upstream by 9bp from the furthest 5'-reaching clone.

The DNA sequence of the resulting clone is set forth as Sequence ID No. 11.

The day 6.5 cDNA library, derived from 6.5 day old mouse embryonic material was prepared from poly A$^+$ selected RNA (by oligo-dT priming), and cloned into the EcoRI site of lambda gt10.

Example V

Isolation and Characterization of XR79

The 550 bp BamHI restriction fragment, including the DNA-binding domain of mouse RAR-beta-encoding DNA (See Hamada et al., Proc. Natl. Acad. Sci. 86: 8289 (1989); incorporated by reference herein) was nick-translated and used to screen a Lambda-ZAP cDNA library comprising a size selected Drosophila genomic library (~2–5 kb, EcoRI restricted) at low stringency. The hybridization mixture contained 35% formamide, 1X Denhardt's, 5X SSPE (1X SSPE=0.15M NaCl, 10 mM $Na_2HPO_4$ 1 mM EDTA), 0.1% SDS, 10% dextran sulfate, 100 mg/ml denatured salmon sperm DNA and $10^6$ cpm of [$^{32}$P]-labelled probe. Duplicate nitrocellulose filters were hybridized for 16h at 42° C., washed once at 25° C for 15 min with 2X SSC (1X SSC=0.15M NaCl, 0.01 M sodium citrate), 0.1% SDS and then washed twice at 55° C. for 30 min. in 2X SSC, 0.1% SDS. The filters were autoradiographed for 3 days at −70° C. using an intensifying screen.

After several rounds of screening, a pure positive clone having an insert of about 3.5 kb is obtained from the Drosophila genomic library. This genomic clone was then used to screen a Drosophila imaginal disc lambda gt10 cDNA library [obtained from Dr. Charles Zuker; see DNA Cloning, A practical approach, Vol I and II, D. M. Glover, ed. (IRL Press (1985)]. Hybridization conditions comprised a hybridization mixture containing 50% formamide, 1X Denhardt's, 5X SSPE, 0.1% SDS, 100 µg/ml denatured salmon sperm DNA and $10^6$ cpm of [$^{32}$P]-labelled probe. Duplicate nitrocellulose filters were hybridized for 16 h at 42° C., washed once at 25° C. for 15 min with 2X SSC (1X SSC=0.15M NaCl, 0.015M sodium citrate), 0.1% SDS and then washed twice at 55° C. for 30 min. in 2X SSC, 0.1% SDS. The filters were autoradiographed for 3 days at −70° C. using an intensifying screen.

Sequence analysis of the positive cDNA clone indicates that this clone encodes another novel member of the steroid/ thyroid superfamily of receptors (designated "XR79", a 2.5 kb cDNA) See Sequence ID No 13 for the DNA sequence of the resulting clone.

The 2.5 kb cDNA encoding XR79 was nick-translated and used as a probe for a nitrocellulose filter containing size-fractionated total RNA, isolated by standard methods from Drosophila melanogaster of different developmental stages. The probe hybridized to a 2.5 kb transcript which was present in RNA throughout development. The levels were highest in RNA from 0–3 hour old embryos and lowest in RNA from second instar larvae. The same 2.5 kb cDNA was nick translated using biotinylated nucleotides and used as a probe for in situ sybridization to whole Drosophila embryos [Tautz and Pfeifle, Chromosoma 98: 81–85 (1989)]. The RNA distribution appeared relatively uniform at different stages of embryogenesis.

Example VI

Sequence Comparisons of Invention Receptors With hRARα, hTRβ, hGR, AND hRXRα

Amino acid sequences of XR1, hRAR-alpha (human retinoic acid receptor-alpha), hTR-beta (human thyroid hormone receptor-beta), hGR (human glucocorticoid receptor), and hRXR-alpha (human retinoid receptor-alpha) were aligned using the University of Wisconsin Genetics Computer Group program "Bestfit" (Devereux et al., supra). The percentage of amino acid identity between RX2 and the other receptors, i.e., in the 66–68 amino acid DNA binding domains and the ligand-binding domains, are summarized in Table 1 as percent amino acid identity.

TABLE 1

Percent amino acid identity between receptor XR1 (verht19) and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 18 | 21 | 45 | 20 |
| hTRβ | 31 | 14 | 59 | 30 |
| hRARα | 32 | 25 | 68 | 27 |
| hRXRα | 29 | 15 | 65 | 22 |

[1]"N-term" = amino terminal domain
[2]"DNA-BD" = receptor DNA binding domain
[3]"Ligand-BD" = receptor ligand binding domain Similarly, the amino acid sequences of invention receptors XR2, XR4, XR5, and XR79 were compared with human RAR-alpha (hRARα), human TR-beta (hTRβ), human glucocorticoid (hGR) and human RXR-alpha (hRXRα). As done in Table 1, the percentage of amino acid identity between the invention receptors and the other receptors are summarized in Tables 2–5, respectively.

TABLE 2

Percent amino acid identity between receptor XR2 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 24 | 21 | 50 | 20 |
| hTRβ | 31 | 19 | 56 | 29 |
| hRARα | 33 | 21 | 55 | 32 |
| hRXRα | 27 | 19 | 52 | 23 |

[1]"N-term" = amino terminal domain
[2]"DNA-BD" = receptor DNA binding domain
[3]"Ligand-BD" = receptor ligand binding domain

TABLE 3

Percent amino acid identity between receptor XR4 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 25 | 24 | 48 | 21 |
| hTRβ | 31 | 21 | 58 | 27 |
| hRARα | 32 | 22 | 62 | 29 |
| hRXRα | 33 | 24 | 62 | 28 |

[1]"N-term" = amino terminal domain
[2]"DNA-BD" = receptor DNA binding domain
[3]"Ligand-BD" = receptor ligand binding domain

TABLE 4

Percent amino acid identity between receptor XR5 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 20 | 20 | 44 | 20 |
| hTRβ | 24 | 14 | 52 | 22 |
| hRARα | 27 | 19 | 59 | 19 |
| hRXRα | 29 | 17 | 61 | 27 |

[1]"N-term" = amino terminal domain
[2]"DNA-BD" = receptor DNA binding domain
[3]"Ligand-BD" = receptor ligand binding domain

TABLE 5

Percent amino acid identity between receptor XR79 and hRARα, TRβ, hGR, and hRXRα

| Comparison receptor | Percent amino acid identity | | | |
|---|---|---|---|---|
| | Overall | N-term[1] | DNA-BD[2] | Ligand-BD[3] |
| hGR | 18 | 22 | 50 | 20 |
| hTRβ | 28 | 22 | 55 | 20 |
| hRARα | 24 | 14 | 59 | 18 |
| hRXRα | 33 | 20 | 65 | 24 |

[1]"N-term" = amino terminal domain
[2]"DNA-BD" = receptor DNA binding domain
[3]"Ligand-BD" = receptor ligand binding domain While the invention has been described in detail with reference to certain preferred embodiments thereof, it will be understood that modifications and variations are within the spirit and scope of that which is described and claimed.

SUMMARY OF SEQUENCES

Sequence ID No. 1 is a nucleotide sequence encoding novel receptor of the present invention designated as "hXR1".

Sequence ID No. 2 is the amino acid sequence deduced from the nucleotide sequence set forth in Sequence ID No 1 (variously referred to herein as receptor "XR1", "hXR1", "hXR1.pep" or "verHT19. pep").

Sequence ID No. 3 is a nucleotide sequence encoding the amino-terminal portion of the novel receptor of the present invention designated as "hXR1prime".

Sequence ID No. 4 is the amino acid sequence deduced from the nucleotide sequence set forth in Sequence ID No. 3 (variously referred to herein as receptor "XR1prime", "hXR1prime", "hXR1prime. pep" or "verHT3 .pep").

Sequence ID No. 5 is a nucleotide sequence encoding the amino-terminal portion of the novel receptor of the present invention designated as "hXR1prim2".

Sequence ID No. 6 is the amino acid sequence deduced from the nucleotide sequence set forth in Sequence ID No. 5 (variously referred to herein as receptor "XR1prim2", "hXR1prim2", "hXR1prim2.pep" or "verHr5.pep").

Sequence ID No. 7 is a nucleotide sequence encoding the novel receptor of the present invention designated as "hXR2".

Sequence ID No. 8 is the amino acid sequence deduced from the nucleotide sequence set forth in Sequence ID NO 7 (variously referred to herein as receptor "XR2", "hXR2" or "hXR2.pep").

Sequence ID No. 9 is a nucleotide sequence encoding novel receptor of the present invention referred to herein as "mXR4".

Sequence ID No. 10 is the amino acid sequence deduced from the nucleotide sequence of Sequence ID No. 9 (variously referred to herein as receptor "XR4", "mXR4" or "mXR4.pep").

Sequence ID No. 11 is the nucleotide sequence encoding the novel receptor of the present invention referred to as "mXR5".

Sequence ID No. 12 is the amino acid sequence deduced from the nucleotide sequence of Sequence ID No. 11 (variously referred to herein as receptor "XR5", "mXR5" or "mXR5.pep").

Sequence ID No. 13 is the nucleotide sequence encoding the novel receptor of the present invention referred to as "dXR79".

Sequence ID No. 14 is the amino acid sequence deduced from the nucleotide sequence of Sequence ID No. 13 (variously referred to herein as "XR79", "dXR79" or "dXR79.pep").

That which is claimed is:

1. DNA encoding a polypeptide characterized by having a DNA binding domain comprising about 66 amino acids with 9 Cys residues, wherein said DNA binding domain is further characterized by the following amino acid sequence identity, relative to the DNA binding domains of hRAR-alpha, hTR-beta, hGR and hRXR-alpha, respectively:

A.
- (i) about 68% amino acid sequence identity with the DNA binding domain of hRAR-alpha;
- (ii) about 59% amino acid sequence identity with the DNA binding domain of hTR-beta;
- (iii) about 45% amino acid sequence identity with the DNA binding domain of hGR; and
- (iv) about 65% amino acid sequence identity with the DNA binding domain of hRXR-alpha; or B.
- (i) about 55% amino acid sequence identity with the DNA binding domain of hRAR-alpha;
- (ii) about 56% amino acid sequence identity with the DNA binding domain of hTR-beta;
- (iii) about 50% amino acid sequence identity with the DNA binding domain of hGR; and
- (iv) about 52% amino acid sequence identity with the DNA binding domain of hRXR-alpha; or C.
- (i) about 62% amino acid sequence identity with the DNA binding domain of hRAR-alpha;
- (ii) about 58% amino acid sequence identity with the DNA binding domain of hTR-beta;
- (iii) about 48% amino acid sequence identity with the DNA binding domain of hGR; and
- (iv) about 62% amino acid sequence identity with the DNA binding domain of hRXR-alpha; or D.
- (i) about 59% amino acid sequence identity with the DNA binding domain of hRAR-alpha;
- (ii) about 52% amino acid sequence identity with the DNA binding domain of hTR-beta;
- (iii) about 44% amino acid sequence identity with the DNA binding domain of hGR; and
- (iv) about 61% amlno acid sequence identity with the DNA binding domain of hRXR-alpha; or E.
- (i) about 59% amino acid sequence identity with the DNA binding domain of hRAR-alpha;
- (ii) about 55% amino acid sequence identity with the DNA binding domain of hTR-beta;
- (iii) about 50% amino acid sequence identity with the DNA binding domain of hGR; and
- (iv) about 65amino acid sequence identity with the DNA binding domain of hRXR-alpha.

2. DNA according to claim 1 wherein the ligand binding domain of said polypeptide is characterized by the following amino acid sequence identity, relative to the ligand binding domains of hRAR-alpha, hTR-beta, hGR and hRXR-alpha, respectively:

A.
- (i) about 27% amino acid sequence identity with the ligand binding domain of hRAR-alpha;
- (ii) about 30% amino acid sequence identity with the ligand binding domain of hTR-beta;
- (iii) about 20% amino acid sequence identity with the ligand binding domain of hGR; and
- (iv) about 22% amino acid sequence identity with the ligand binding domain of hRXR-alpha; or B.
- (i) about 32% amino acid sequence identity with the ligand binding domain of hRAR-alpha;
- (ii) about 29% amino acid sequence identity with the ligand binding domain of hTR-beta;
- (iii) about 20% amino acid sequence identity with the ligand binding domain of hGR; and
- (iv) about 23% amino acid sequence identity with the ligand binding domain of hRXR-alpha; or C.
- (i) about 29% amino acid sequence identity with the ligand binding domain of hRAR-alpha;
- (ii) about 27% amino acid sequence identity with the ligand binding domain of hTR-beta;
- (iii) about 21% amino acid sequence identity with the ligand binding domain of hGR; and
- (iv) about 28% amino acid secuence identity with the ligand binding domain of hRXR-alpha; or D.
- (i) about 19% amino acid sequence identity with the ligand binding domain of hRAR-alpha;
- (ii) about 22% amino acid sequence identity with the ligand binding domain of hTR-beta;
- (iii) about 20% amino acid sequence identity with the ligand binding domain of hGR; and
- (iv) about 27% amino acid sequence identity with the ligand binding domain of hRXR-alpha; or E.
- (i) about 18% amino acid sequence identity with the ligand binding domain of hRAR-alpha;
- (ii) about 20% amino acid sequence identity with the ligand binding domain of hTR-beta;
- (iii) about 20% amino acid sequence identity with the ligand binding domain of hGR; and
- (iv) about 24% amino acid sequence identity with the ligand binding domain of hRXR-alpha.

3. DNA according to claim 1 wherein said polypeptide has an overall amino acid sequence identity, relative to hRAR-alpha, hTR-beta, hGR and hRXR-alpha, respectively of:

A.
- (i) about 32% relative to hRAR-alpha;
- (ii) about 31% relative to hTR-beta;
- (iii) about 18% relative to hGR; and
- (iv) about 29% relative to hRXR-alpha; or B.
- (i) about 33% relative to hRAR-alpha;

(ii) about 31% relative to hTR-beta;
(iii) about 24% relative to hGR; and
(iv) about 27% relative to hRXR-alpha; or C.
(i) about 32% relative to hRAR-alpha;
(ii) about 31% relative to hTR-beta;
(iii) about 25% relative to hGR; and
(iv) about 33% relative to hRXR-alpha; or D.
(i) about 27% relative to hRAR-alpha;
(ii) about 24% relative to hTR-beta;
(iii) about 20% relative to hGR; and
(iv) about 29% relative to hRXR-alpha; or E.
(i) about 24% relative to hRAR-alpha;
(ii) about 28% relative to hTR-beta;
(iii) about 18% relative to hGR; and
(iv) about 33% relative to hRXR-alpha.

4. DNA according to claim 1 wherein said polypeptide is characterized by having a DNA binding domain comprising:
(i) about 68% amino acid sequence identity with the DNA binding domain of hRAR-alpha;
(ii) about 59% amino acid sequence identity with the DNA binding domain of hTR-beta;
(iii) about 45% amino acid sequence identity with the DNA binding domain of hGR; and
(iv) about 65% amino acid sequence identity with the DNA binding domain of hRXR-alpha.

5. DNA according to claim 1 wherein said polypeptide is characterized by having a DNA binding domain comprising:
(i) about 55% amino acid sequence identity with the DNA binding domain of hRAR-alpha;
(ii) about 56% amino acid sequence identity with the DNA binding domain of hTR-beta;
(iii) about 50% amino acid sequence identity with the DNA binding domain of hGR; and
(iv) about 52% amino acid sequence identity with the DNA binding domain of hRXR-alpha.

6. DNA according to claim 1 wherein said polypeptide is characterized by having a DNA binding domain comprising:
(i) about 62% amino acid sequence identity with the DNA binding domain of hRAR-alpha;
(ii) about 58% amino acid sequence identity with the DNA binding domain of hTR-beta;
(iii) about 48% amino acid sequence identity with the DNA binding domain of hGR; and
(iv) about 62% amino acid sequence identity with the DNA binding domain of hRXR-alpha.

7. DNA according to claim 1 wherein said polypeptide is characterized by having a DNA binding domain comprising:
(i) about 59% amino acid sequence identity with the DNA binding domain of hRAR-alpha;
(ii) about 52% amino acid sequence identity with the DNA binding domain of hTR-beta;
(iii) about 44% amino acid sequence identity with the DNA binding domain of hGR; and
(iv) about 61% amino acid sequence identity with the DNA binding domain of hRXR-alpha.

8. DNA according to claim 1 wherein said polypeptide is characterized by having a DNA binding domain comprising:
(i) about 59% amino acid sequence identity with the DNA binding domain of hRAR-alpha;
(ii) about 55% amino acid sequence identity with the DNA binding domain of hTR-beta;
(iii) about 50% amino acid sequence identity with the DNA binding domain of hGR; and
(iv) about 65% amino acid sequence identity with the DNA binding domain of hRXR-alpha.

9. DNA according to claim 1 wherein the nucleotide sequence of said DNA is selected from:
the nucleotide sequence set forth in Sequence ID No. 1,
the combination of Sequence ID No. 3 and the continuation thereof comprising nucleotides 349–1952 as set forth in Sequence ID No. 1,
the combination of Sequence ID No. 5 and the continuation thereof comprising nucleotides 352–1952 as set forth in
Sequence ID No. 1,
Sequence ID No. 7,
Sequence ID No. 9,
Sequence ID No. 11, or
Sequence ID No. 13.

10. An expression vector comprising DNA according to claim 1, and further comprising:
at the 5'-end of said DNA, a promoter and a triplet encoding a translational start codon, and
at the 3'-end of said DNA, a triplet encoding a translational stop codon;
wherein said expression vector is operative in an animal cell in culture to express the protein encoded by the continuous sequence of amino acid-encoding triplets.

11. An animal cell in culture transformed with an expression vector according to claim 10.

12. A method of making a polypeptide comprising culturing the cells of claim 11 under conditions suitable for the expression of said polypeptide.

13. A DNA or RNA labeled for detection; wherein said DNA or RNA comprises a nucleic acid segment of at least 20 bases in length, wherein said segment has substaintially the same sequence as a segment of the same length selected from the DNA segment represented by:
bases 21–1902, inclusive, of Sequence ID No. 1;
bases 1–386, inclusive, of Sequence ID No. 3;
bases 10–300, inclusive, of Sequence ID No. 5;
bases 21–1615, inclusive, of Sequence ID No. 7;
bases 21–2000, inclusive, of Sequence ID No. 9;
bases 1–2450, inclusive, of Sequence ID No. 11;
bases 21–2295, inclusive, of Sequence ID No. 13;
or the complement of any one of said segment.

14. DNA encoding a chimeric receptor comprising at least an amino-terminal domain, a DNA-binding domain, and a ligand-binding domain,
wherein at least one of the domains thereof is derived from a polypeptide characterized by having a DNA binding domain comprising about 66 amino acids with 9 Cys residues, wherein said DNA binding domain is further characterized by the following amino acid sequence identity, relative to the DNA binding domains of hRAR-alpha, hTR-beta, hGR and hRXR-alpha, respectively:

A.
(i) about 68% amino acid sequence identity with the DNA binding domain of hRAR-alpha;
(ii) about 59% amino acid sequence identity with the DNA binding domain of hTR-beta;

(iii) about 45% amino acid sequence identity with the DNA binding domain of hGR; and
(iv) about 65% amino acid sequence identity with the DNA binding domain of hRXR-alpha; or B.
(i) about 55% amino acid sequence identity with the DNA binding domain of hRAR-alpha;
about 56% amino acid sequence identity with the DNA binding domain of hTR-beta;
(iii) about 50% amino acid sequence identity with the DNA binding domain of hGR; and
(iv) about 52% amino acid sequence identity with the DNA binding domain of hRXR-alpha; or C.
(i) about 62% amino acid sequence identity with the DNA binding domain of hRAR-alpha;
(ii) about 58% amino acid sequence identity with the DNA binding domain of hTR-beta;
(iii) about 48% amino acid sequence identity with the DNA binding domain of hGR; and
(iv) about 62% amino acid sequence identity with the DNA binding domain of hRXR-alpha; or D.
(i) about 59% amino acid sequence identity with the DNA binding domain of hRAR-alpha;
(ii) about 52% amino acid sequence identity with the DNA binding domain of hTR-beta;
(iii) about 44% amino acid sequence identity with the DNA binding domain of hGR; and
(iv) about 61% amino acid sequence identity with the DNA binding domain of hRXR-alpha; or E.
(i) about 59% amino acid sequence identity with the DNA binding domain of hRAR-alpha;
(ii) about 55% amino acid sequence identity with the DNA binding domain of hTR-beta
(iii) about 50% amino acid sequence identity with the DNA binding domain of hGR; and
(iv) about 65% amino acid sequence identity with the DNA binding domain of hRXR-alpha;

and wherein at least one of the domains thereof is derived from at least one previously identified member of the steroid/thyroid superfamily of receptors.

\* \* \* \* \*